(12) United States Patent
Dekel

(10) Patent No.: US 11,523,753 B2
(45) Date of Patent: Dec. 13, 2022

(54) HEAD TRACKING FRAME FOR DENTAL NAVIGATION

(71) Applicant: CLARONAV INC., North York (CA)

(72) Inventor: Doron Dekel, Toronto (CA)

(73) Assignee: CLARONAV INC., North York (CA)

(*) Notice: Subject to any disclaimer, the term of this patent is extended or adjusted under 35 U.S.C. 154(b) by 982 days.

(21) Appl. No.: 16/268,580

(22) Filed: Feb. 6, 2019

(65) Prior Publication Data
US 2019/0239776 A1    Aug. 8, 2019

Related U.S. Application Data

(60) Provisional application No. 62/627,357, filed on Feb. 7, 2018.

(51) Int. Cl.
| | |
|---|---|
| *A61B 5/11* | (2006.01) |
| *A61C 19/045* | (2006.01) |
| *G06F 3/01* | (2006.01) |
| *A61B 34/20* | (2016.01) |
| *A61C 1/08* | (2006.01) |

(52) U.S. Cl.
CPC ............ *A61B 5/1114* (2013.01); *A61B 34/20* (2016.02); *A61C 19/045* (2013.01); *G06F 3/012* (2013.01); *A61C 1/082* (2013.01)

(58) Field of Classification Search
CPC ... A61B 5/1114; A61B 5/4542; A61B 5/6803; A61C 19/045
USPC ..................................................... 433/68–69
See application file for complete search history.

(56) References Cited

U.S. PATENT DOCUMENTS

| | | | |
|---|---|---|---|
| 4,034,474 A | 7/1977 | Lee | |
| 4,537,574 A * | 8/1985 | Clark | A61C 11/022 |
| | | | 433/69 |
| 4,673,352 A | 6/1987 | Hansen | |
| (Continued) | | | |

FOREIGN PATENT DOCUMENTS

| | | | | |
|---|---|---|---|---|
| CN | 106997107 A | * | 8/2017 | |
| CN | 107049312 A | * | 8/2017 | ............ A61B 5/398 |
| (Continued) | | | | |

OTHER PUBLICATIONS

English translation of CN 106997107 A (Year: 2017).*
(Continued)

*Primary Examiner* — Daniel L Cerioni
*Assistant Examiner* — Raymond P Dulman
(74) *Attorney, Agent, or Firm* — Bereskin & Parr LLP/S.E.N.C.R.L., s.r.l.

(57) ABSTRACT

Systems and methods of tracking a head of a patient are provided. The system includes a motion tracking system and a head tracker. The head tracker includes a frame, at least one trackable target coupled to the frame, at least one nose pad coupled to the frame, and a pair of adjustable ear coupling members coupled to the frame and shaped for engaging with at least a portion of a back surface of an ear of the patient. The head tracker is configured to apply a clamping force to hold the trackable target in a stable spatial relationship with a location of interest in the head. The motion tracking system includes a sensor for tracking the trackable target and a processor configured for determining a position of the location of interest from the position and orientation of the trackable target and the stable spatial relationship.

20 Claims, 15 Drawing Sheets

(56) References Cited

U.S. PATENT DOCUMENTS

| | | | |
|---|---|---|---|
| 4,836,778 | A | 6/1989 | Baumrind et al. |
| 5,829,444 | A | 11/1998 | Ferre et al. |
| 5,967,980 | A | 10/1999 | Ferre et al. |
| 6,640,127 | B1 | 10/2003 | Kosaka et al. |
| 7,182,737 | B2 | 2/2007 | Kim et al. |
| 9,125,624 | B2 | 9/2015 | Dekel et al. |
| 9,402,691 | B2 | 8/2016 | Merritt et al. |
| 2005/0049486 | A1 | 3/2005 | Urquhart et al. |
| 2007/0253541 | A1 | 11/2007 | Sukovic et al. |
| 2013/0322719 | A1 | 12/2013 | Dekel et al. |
| 2016/0287173 | A1 * | 10/2016 | Abreu .................... G02C 11/10 |

FOREIGN PATENT DOCUMENTS

| | | | | |
|---|---|---|---|---|
| DE | 202016100240 U1 * | 3/2016 | ........... | A61C 19/045 |
| WO | WO-2015100499 A1 * | 7/2015 | ........... | A61B 5/0478 |

OTHER PUBLICATIONS

English translation of CN 107049312 A (Year: 2017).*
English translation of DE 202016100240 U1 (Year: 2016).*
International Search Report and Written Opinion in respect of PCT/CA2019/050150 dated Jun. 5, 2019.

* cited by examiner

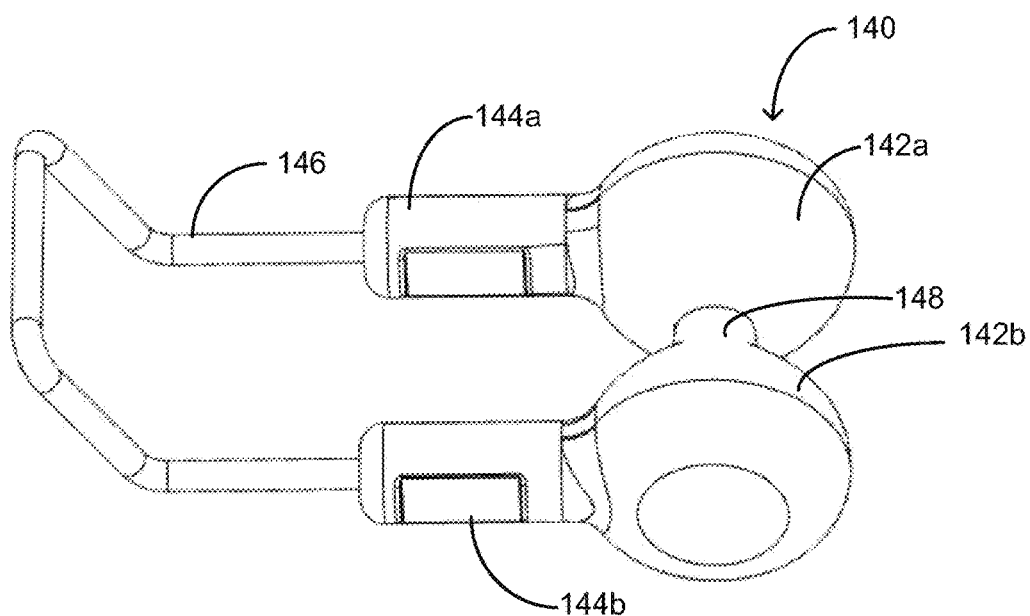
FIG. 9A
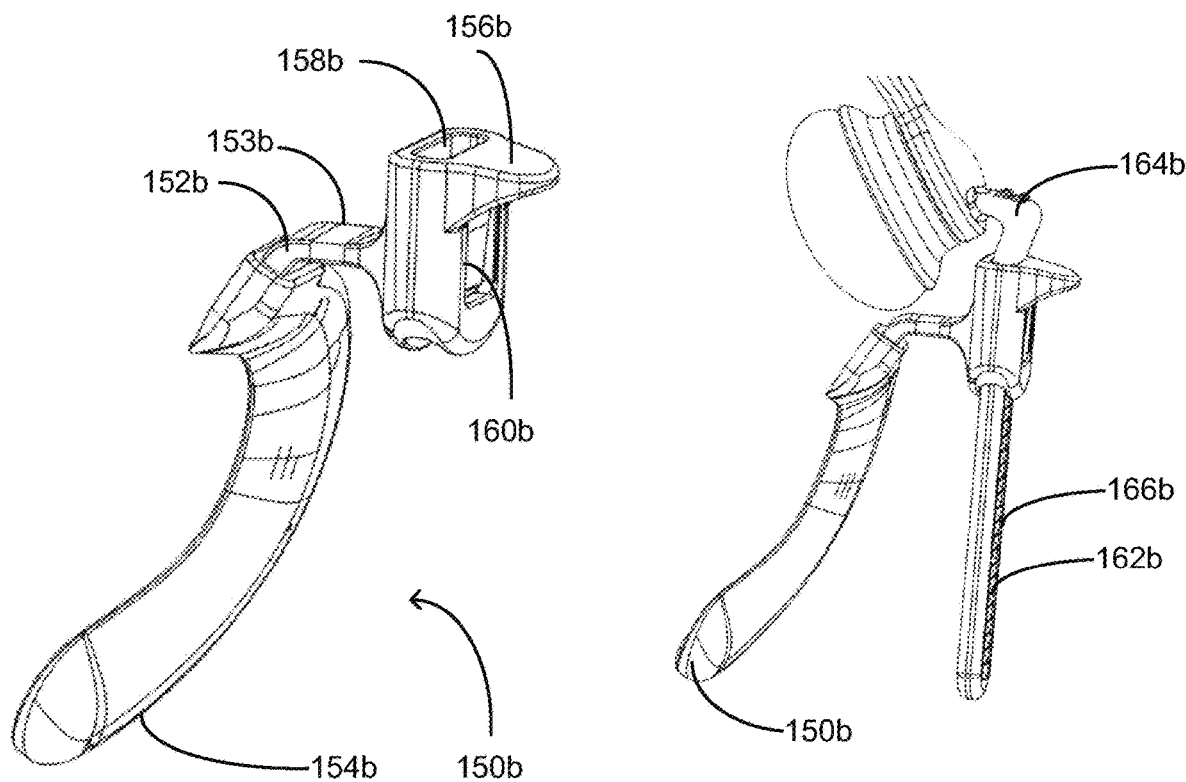
FIG. 9C  FIG. 9B

HEAD TRACKING FRAME FOR DENTAL NAVIGATION

PRIORITY

This application claims the benefit of U.S. Provisional Patent Application No. 62/627,357, filed Feb. 7, 2018, which is incorporated herein by reference in its entirety.

FIELD

The described embodiments relate to the field of dentistry, in particular, the field of dental navigation systems.

INTRODUCTION

Dental navigation systems are increasingly common and commercially available. Many existing dental navigation systems, such as that described in U.S. Pat. Nos. 9,125,624 and 9,402,691 include an optical tracking system to track the motions of the patient's jaw during dental surgery, usually by processing the video stream of a calibrated stereoscopic camera. However, it can be challenging to optically track the jaw directly, due to line of sight interruptions and various other reasons. Thus, existing dental navigation systems incorporate a retainer appliance, rigidly coupled to the jaw surface, to provide jaw tracking by an optically marked surface positioned outside the mouth, where it can be easily tracked by the optical tracking system. The coupling of the retainer appliance to the jaw requires time, skill, and costs for disposable moldable parts. Furthermore, to provide a stable and retentive attachment to the jaw, the retainer appliance blocks part of the mouth opening and covers part of the jaw surface, both of which can impede the ease of performing the dental surgery.

Means for tracking the upper jaw using a head frame are primarily used for the purpose of measuring the motions of the upper and lower jaws relative to each other. Examples of such approaches are described in U.S. Pat. Nos. 4,034,474, 4,673,352, 4,836,778, 5,967,980 and 7,182,737. Such head frames typically involve a strap around the back of the patient's head or plugs pressed into the patient's ear canals.

However, such head frames are not optimal for dental navigation in several aspects. For example, the head frame can move relative to the head due to movement of the patient's lower jaw, changes in the patient's facial expression (e.g., wincing and blinking), and/or movement of the patient's head relative to the head support provided by a dental chair. As well, these head frames can impede hand and arm movements by a user (i.e., dentist, surgeon,) around the patient's cheeks and temples. Furthermore, the pressure of plugs in the patient's ear canal can cause discomfort for the patient.

SUMMARY

The various embodiments described herein generally relate to systems and methods for tracking a head of a patient. An example system for tracking a head of a patient includes a motion tracking system and a head tracker. The head tracker includes: a frame having a front arm and two side arms, at least one trackable target coupled to the frame, at least one nose pad coupled to the front arm of the frame, and a pair of adjustable ear coupling members shaped for engaging with at least a portion of a back surface of an ear of the patient. The two side arms are spaced apart to accommodate the width of the patient's head between the side arms. A position and orientation of the at least one trackable target is determinable by the motion tracking system tracking the target. The at least one nose pad defines at least one nose pad contact surface for engaging with a nasion region of the patient. Each ear coupling member is coupled to a respective side arm. The head tracker is configured to apply a clamping force to pull the at least one nose pad rearwardly to hold the nose pad contact surface against the nasion region of the patient and to pull the pair of adjustable ear coupling members forwardly to hold the ear coupling members against the back surfaces of the ears of the patient, to hold the at least one trackable target in a stable spatial relationship with a location of interest in the head of the patient. The motion tracking system includes a sensor for tracking the at least one trackable target and a processor configured for determining a position of the location of interest in the head of the patient from the position and orientation of the at least one trackable target of the head tracker and the stable spatial relationship.

In at least one embodiment, the frame can be configured to not overlay each of the patient's eyes, eyebrows, and temples when the head tracker is mounted on the patient's head.

In at least one embodiment, the frame can include a coupling portion for coupling each of the front arm and two side arms. The two side arms can extend from the coupling portion at substantially opposite directions, and the front arm can extend from the coupling portion substantially perpendicular to each of the two side arms.

In at least one embodiment, the coupling portion can be configured to be located above at least one of the top of the patient's head and the patient's forehead when the head tracker is mounted on the patient's head.

In at least one embodiment, the frame can further include an adjusting mechanism for adjusting a pose of at least a portion of the front arm relative to the two side arms. Adjusting the pose of the portion of the front arm can vary a distance between the at least one nose pad and at least one ear coupling member of the pair of ear coupling members.

In at least one embodiment, the frame can further include a hinge for coupling at least a portion of the front arm to the frame. Rotation of the at least a portion of the front arm around the hinge can be configured to vary a distance between the at least one nose pad and at least one ear coupling member of the pair of ear coupling members.

In at least one embodiment, the frame can further include at least one head cushion coupled to at least one side arm of the two side arms for engaging with at least a portion of the patient's head when the head tracker is mounted on the patient's head.

In at least one embodiment, the at least one head cushion can include a material that is deformable to enable the head cushion to adapt its surface to the shape of the at least a portion of the patient's head and that can resist a deformation following the application and immediate removal of a force of up to about 5 Newtons to the side arm.

In at least one embodiment, the clamping force applied by the head tracker can be adjustable such that a distance between the position of the location of interest determined by the motion tracking system and the actual location of interest in the head varies by less than 1 millimeter when the head tracker is mounted on the patient's head and at least one of the patient's facial expression changes and the patient's mouth moves.

In at least one embodiment, the clamping force applied by the head tracker can be adjustable such that a distance between the position of the location of interest determined by the motion tracking system and the actual location of interest in the head varies by less than 1 millimeter following the application and immediate removal of a force of up to about 5 Newtons to any part of the frame in any direction when the head tracker is mounted on the patient's head.

In at least one embodiment, the the clamping force applied by the head tracker can be configurable to apply a rearward force in the range of about 1 to 4 Newtons against the nasion region of the patient when the head tracker is mounted on the patient's head and when the patient's head is between 5th and 95th percentiles in each of width, length, and height dimensions for an adult head.

In at least one embodiment, the head tracker can further include, for each side arm, a biasing member for applying the clamping force, the biasing member comprising at least one of an elastic member and a spring member.

In at least one embodiment, each adjustable ear coupling member can include rubber padding defining at least one ear coupling contact surface for engaging with the at least a portion of a back surface of the ear of the patient.

In at least one embodiment, the at least one nose pad can include at least two adjustable nose pads, an orientation of each nose pad being independently adjustable relative to the frame.

In at least one embodiment, the frame can further include a nose pad attachment member for adjustably coupling the at least one nose pad to the frame.

In at least one embodiment, the nose pad attachment member can include a pliable metal wire.

In at least one embodiment, the at least one trackable target coupled to the frame can comprise at least one high contrast optical target marked on a surface of at least one of the front arm and the two side arms.

An example method for tracking the head of a patient involves providing a head tracker including a frame, at least one nose pad coupled to the frame, a pair of adjustable ear coupling members coupled to the frame, and at least one trackable target coupled to the frame, the at least one nose pad defining at least one nose pad contact surface; positioning the head tracker on the patient's head by engaging the at least one nose pad contact surface with a nasion region of the patient; positioning the pair of adjustable ear coupling members behind the ears of the patient; and adjusting a clamping force applied by the head tracker to hold the at least one trackable target in a stable spatial relationship with a location of interest in the head of the patient. The clamping force is configured to pull the nose pad rearwardly to hold the nose pad contact surface against the nasion region of the patient and to pull the pair of adjustable ear coupling members forwardly to hold the ear coupling members against the back surfaces of the ears of the patient.

In at least one embodiment, the method also involves determining a position and orientation of the at least one trackable target by operating a motion tracking system to track the at least one trackable target; and determining a position of the location of interest in the head of the patient from the position and orientation of the at least one trackable target of the head tracker and the stable spatial relationship.

BRIEF DESCRIPTION OF THE DRAWINGS

Several embodiments will now be described in detail with reference to the drawings, in which:

FIG. 9A is an example illustration of at least one nose pad of the head tracker of FIG. 2;

FIG. 9B is an example illustration of an adjustable ear coupling member of the head tracker of FIG. 2;

FIG. 9C is an example illustration of the adjustable ear coupling member of FIG. 9B coupled to a side arm of the head tracker of FIG. 2;

Figure 1:
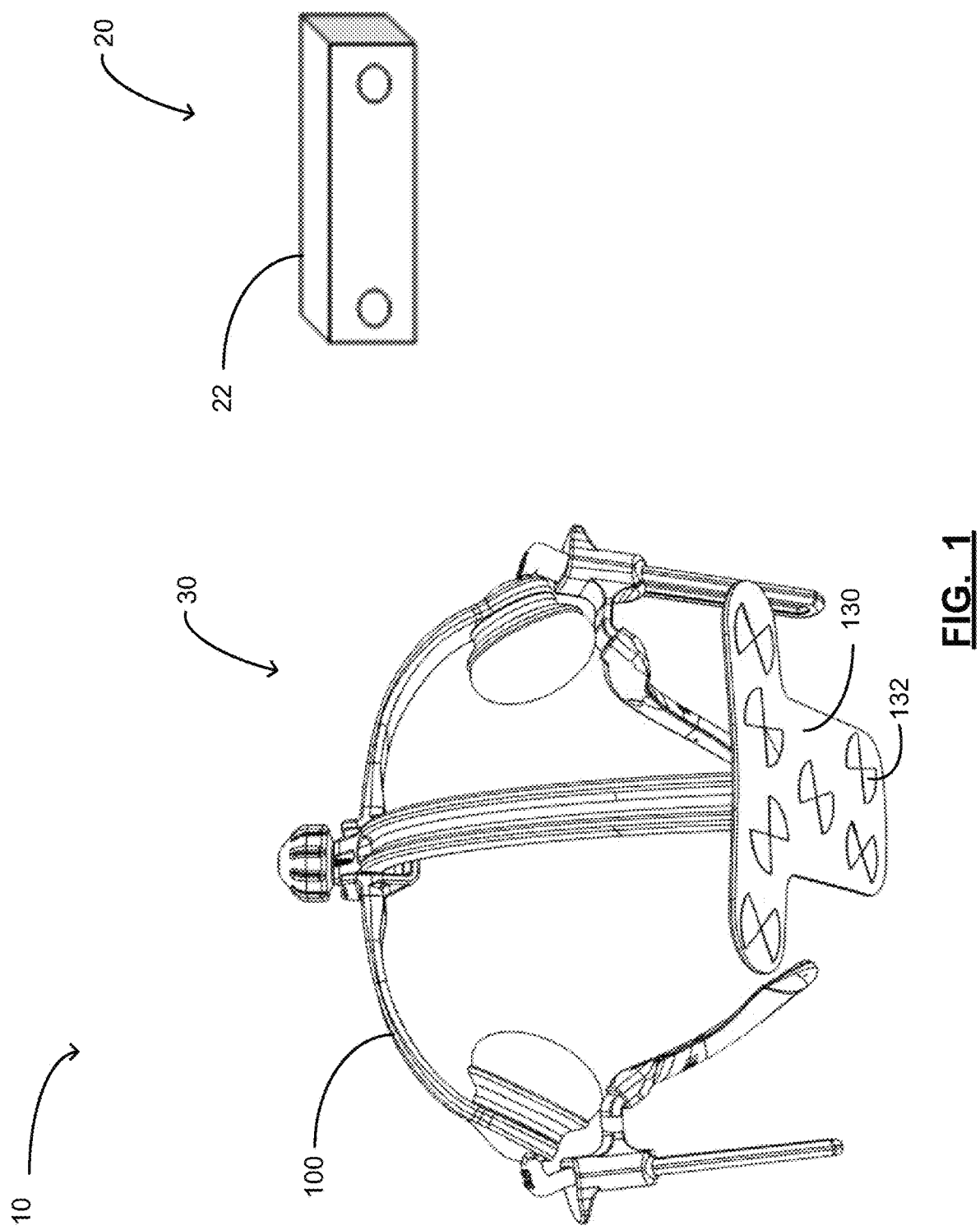
FIG. 1 is an example illustration of a system for tracking a head of a patient, according to at least one embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

In some embodiments, aspects of methods described herein, such as method 300 described with reference to FIG. 14 below, may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication component. For example and without limitation, the programmable computer (referred to below as data processor) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication component may be a network communication interface. In embodiments in which elements are combined, the communication component may be a software communication interface, such as those for inter-process communication (IPC). In still other embodiments, there may be a combination of communication components implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Referring now to FIG. 1, shown therein is an example illustration of a system 10 for tracking a head of a patient, according to at least one embodiment. The system 10 includes a motion tracking system 20 and a head tracker 30. The motion tracking system 20 may also be referred to as an external tracking system or a pose tracking system.

The head tracker 30 includes a frame 100 and at least one trackable target 130 coupled to the frame 100. The head tracker 30 can be positioned or mounted on a patient's head to hold the at least one trackable target 130 in a stable spatial relationship with a location of interest in the head of the patient. That is, the frame 100 can hold the at least one trackable target 130 in a stable spatial relationship with the location of interest in the head of the patient. The location of interest to the user of the navigation system in the head of the patient during the surgery can be anywhere on or inside the skull, for example a location on or inside the upper jaw of the patient. The position and orientation of the at least one trackable target 130 is determinable by the motion tracking system 20 tracking the at least one trackable target 130.

The motion tracking system 20 can track the position and orientation of the at least one trackable target 130 and use the stable spatial relationship between the at least one trackable target 130 and the location of interest in the head of the patient to track the position of the location of interest in the head of the patient even while the head is moving or rotating. The motion tracking system 20 can track the at least one trackable target 30 at a sufficiently high accuracy and sufficiently low latency for the targeted application of the system 10.

The motion tracking system 20 includes a sensor, such as detection device 22, for tracking the at least one trackable target 130, and a processor (not shown in FIG. 1) operatively coupled to the detection device 22. The motion tracking system 20 can also include a computer-readable memory operatively coupled to the processor. The processor of the motion tracking system 20 can be configured for determining the position and orientation of the location of interest in the head of the patient from a position and orientation of the at least one trackable target 130 of the head tracker 30.

In some embodiments, the motion tracking system 20 can be an optical tracking system, for example, the MicronTracker™ by ClaroNav™ Inc. In at least one embodiment, the detection device 22 can be a stereoscopic video camera. When the motion tracking system 20 is an optical tracking system, the at least one trackable target 130 can include high contrast optical markings 132 as shown in FIG. 1. The at least one trackable target 130 can be referred to as an "optical marker" when it includes high contrast optical markings 132. Although FIG. 1 shows seven high contrast optical markings 132 on the trackable target 130, in some embodiments, the at least one trackable target 130 can include fewer or more high contrast optical markings 132.

In at least one embodiment, the at least one trackable target 130 can include one or more retro-reflective regions and the optical tracking system can include a tracking camera and a source of illumination placed near the lenses of the tracking camera such that a contrast between the surface of the retro-reflective region and the surrounding surfaces is created in the camera's image. The one or more retro-reflective regions can have any appropriate shape, including a spherical shape. In other embodiments, a magnetic tracking system may be used and the at least one trackable target 130 may contain a magnetic field sensing coil. In some embodiments, the motion tracking system 20 may be an electromagnetic tracking system.

Figure 2:
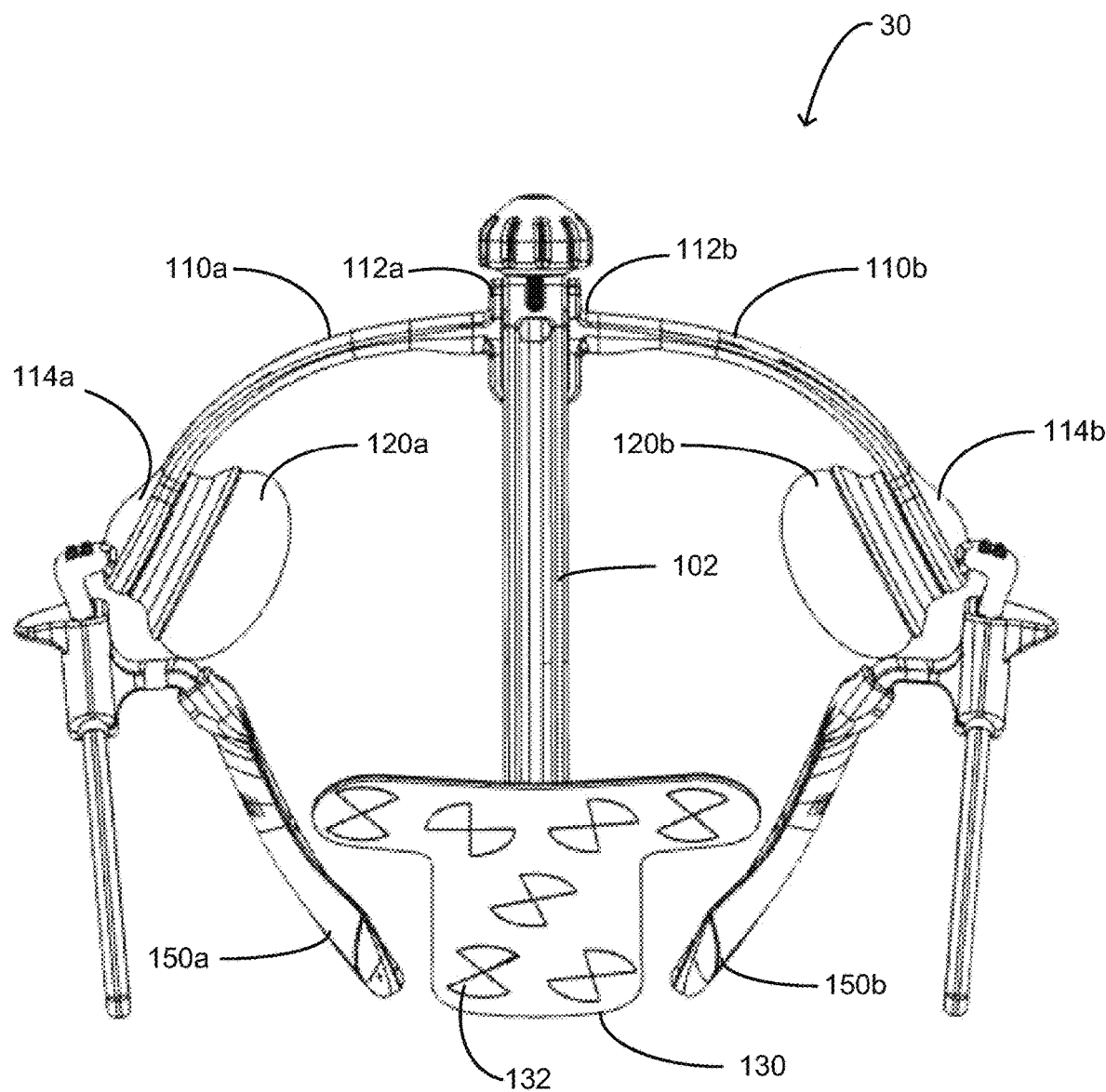
FIG. 2 is an example illustration of a front view of a head tracker of the system of FIG. 1, according to at least one embodiment.
Figure 3:
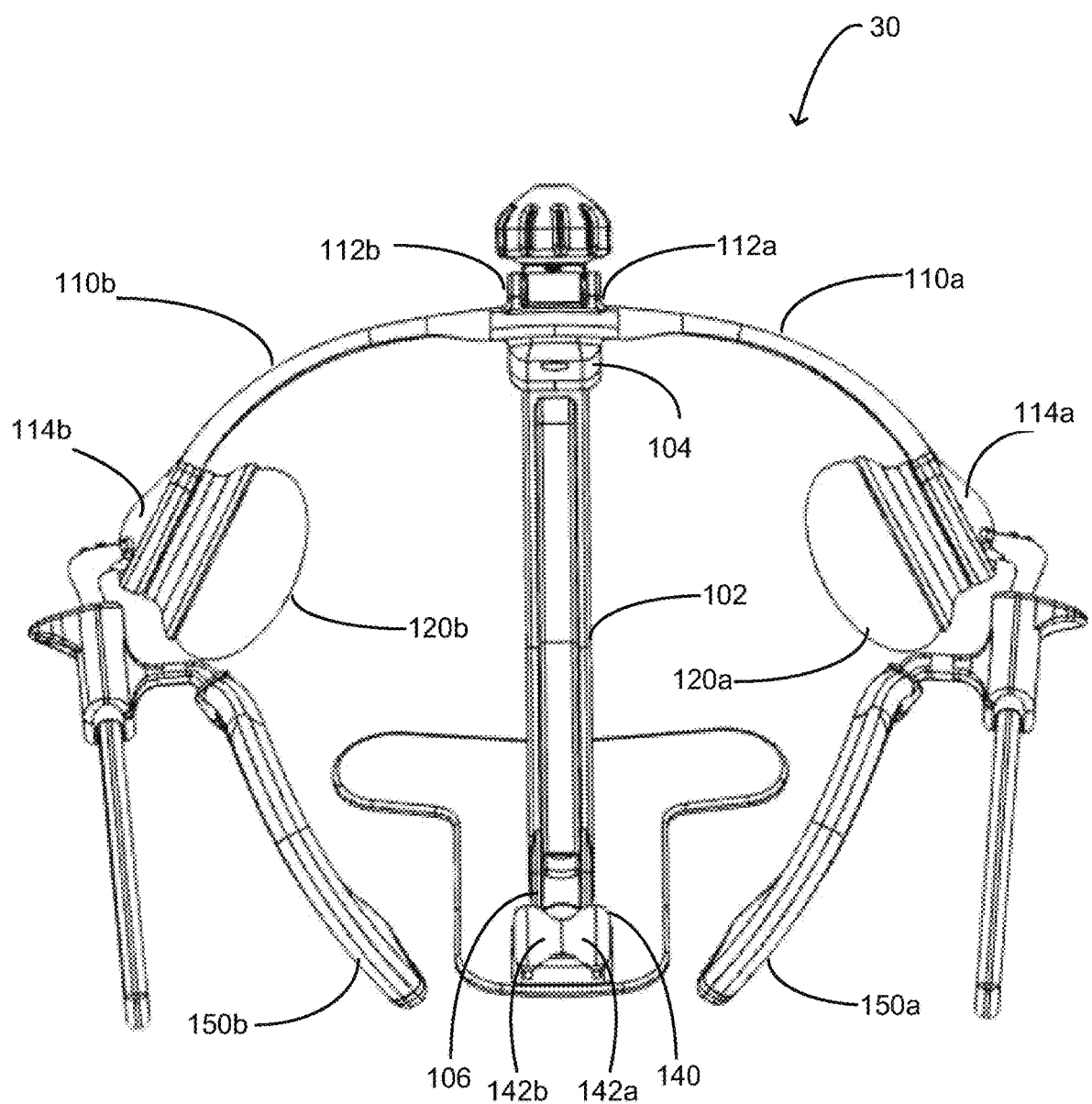
FIG. 3 is an example illustration of a rear view of the head tracker of FIG. 2.

Referring now to FIGS. 2 and 3, shown therein are example illustrations of a front view and a rear view of the head tracker 30, according to at least one embodiment. The head tracker 30 includes the frame 100, the at least one trackable target 130, at least one nose pad 140 (shown in FIG. 3), and a pair of adjustable ear coupling members 150.

The frame 100 of the head tracker 30 includes a front arm 102 and two side arms 110 coupled to the front arm 102. The front arm 102 may also be referred to as a front member. As shown in FIG. 3, the front arm 102 can have a proximal portion 104 and a distal portion 106. The front arm 102 is coupled to the frame 100 at the proximal portion 104 of the front arm 102. Since the front arm 102 of head tracker 30 extends downwardly, the proximal portion 104 can also be referred to as an upper portion of the front arm 102 and the distal portion 106 can also be referred to as a lower portion of the front arm 102.

The two side arms 110 include a right arm 110*a* and a left arm 110*b*. The side arms 110 are spaced apart to accommodate a width of a patient's head between the side arms 110. Each side arm 110*a*, 110*b* has a proximal portion 112*a*, 112*b* (herein collectively referred to as the proximal portions 112 of the side arms 110) and a distal portion 114*a*, 114*b* (herein collectively referred to as the distal portions 112 of the side arms 110), respectively. Each side arm 110*a*, 110*b* is coupled to the frame 100 at the proximal portion 112*a*, 112*b* of the respective side arm 110*a*, 110*b*. Since the side arms 110 of head tracker 30 extend downwardly, the proximal portions 112 can also be referred to as upper portions of side arms 110 and the distal portions 114 can also be referred to as a lower portions of the side arms 110.

The frame 100 can include a coupling portion for coupling the front arm 102 and the side arms 110. In particular, the coupling portion can include the proximal portion 104 of the front arm 102 and the proximal portions 112 of the side arms 110. As shown in FIG. 2, the coupling portion can be configured to be located above the top of the patient's head when the head tracker 30 is mounted on the patient's head.

When the coupling portion is configured to be located above the top of the patient's head, the coupling portion does not overlay any one of the patient's eyes, eyebrows, and temples when the head tracker 30 is mounted on the patient's head. By not overlaying or covering these areas of the patient's face, the frame 100, including the coupling portion, can be configured to allow for unimpeded or unobstructed hand and arm movements by a user (i.e., surgeon, dentist) who may be seated behind the patient's head during dental surgery. In particular, the frame 100 can be configured to allow for unimpeded hand and arm movements around the patient's cheeks and temples when accessing the oral cavity.

It should be noted that FIGS. 1 to 7 are provided for illustration purposes and other configurations are possible. For example, other configurations for the frame 100 to not overlay the patient's eyes, eyebrows, and temples are possible. Instead of the coupling portion being configured to be located, or routed above the top of the patient's head, in at least one embodiment, the coupling portion can be configured to be located above the patient's forehead when the head tracker 30 is mounted on a patient's head.

As described above, the head tracker 30 includes the trackable target 130 coupled to the frame 100. As shown in FIG. 3, the trackable target 130 can be coupled to the front arm 102 of the frame 100. More specifically, the trackable target 130 can be coupled to the distal portion 106 of the front arm 102. The trackable target 130 can include a plate on which the high contrast optical markings 132 are located. FIGS. 1 to 7 are provided for illustration purposes and other configurations are possible. For example, additional trackable targets 130 can be provided, trackable targets 130 can be attached to any location on the frame 100, and/or trackable targets 130 can be marked directly on a region of the surface of the frame 100, such as the surface of any one of the front arm 102 and the side arms 110. In at least one embodiment, at least one high contrast optical targets 132 can be marked on a surface of at least one of the front arm 102 and the two sides arms 110.

The head tracker 30 includes a pair of adjustable ear coupling members 150. In particular, the head tracker 30 includes a right adjustable ear coupling member 150*a* and a left adjustable ear coupling member 150*b* (herein collectively referred to as the adjustable ear coupling members 150 or the ear coupling members 150). The adjustable ear coupling members 150 are shaped for engaging with at least a portion of a back surface of an ear of the patient. As shown in FIGS. 2 and 3, the adjustable ear coupling members 150 can be coupled to the distal portions 114 of the respective side arms 110.

The head tracker 30 also includes a nose pad 140 (shown in FIG. 3) that defines two nose pad contact surfaces, that is, a right nose pad contact surface 142*a* and a left nose pad contact surface 142*b* (herein collectively referred to as nose pad contact surfaces 142) for engaging with a nasion region of the patient when the head tracker 30 is mounted on the patient's head. For example, the two nose pad contact surfaces 142 can engage with two opposing sides of the nasion region of the patient. The nose pad 140 is be coupled to the front arm 102 of the frame 100. More specifically, the nose pad 140 can be coupled to the distal portion 106 of the front arm 102, as shown in FIG. 3.

Again, FIGS. 1 to 7 are provided for illustration purposes and other configurations are possible. For example, additional nose pads can be provided. In at least one embodiment, a head tracker can include two nose pads, each nose pad defining a nose pad contact surface for engaging with the nasion region of the patient. In at least one embodiment, a head tracker can include two nose pads, each nose pad defining a nose pad contact surface for engaging with one of two opposing sides of the nasion region of the patient.

In some embodiments, the system 10 can also include a registration computer configured for determining a registration of the head of the patient with a volumetric image of the head obtained by a computed tomography (CT) or magnetic resonance imaging (MRI) scanner and stored in a computer-readable memory. Registration is typically performed at the start of surgery. Registration aligns the head of the patient with the image of the head so that the image of the head can be used as a map or visual aid to guide the placement of surgical instruments and implants at locations of interest in the head during surgery. To align the head of the patient with the image of the head, a coordinate transform for mapping a reference coordinate space associated with the head to a reference coordinate space associated with the image is determined.

In various embodiments, the registration computer can be operatively coupled to the motion tracking system 20. The system 10 may be distributed over a wide geographic area and the registration computer can communicate with the motion tracking system 20 via a network (not shown). The system 10 can include any appropriate communication component (not shown) to provide access to the network or enable communication between devices and systems.

In some embodiments, the registration computer can be integrated into the motion tracking system 20 to provide an integrated system configured for measuring changes to the pose of the at least trackable target 130 and, based on these changes to the pose of the at least trackable target 130, determining the registration of the head with the volumetric image of the head stored in a memory.

As shown in FIGS. 2 and 3, the head tracker 30 can also include a right head cushion 120a and a left head cushion 120b (herein collectively referred to as the head cushions 120) for engaging with at least a portion of the patient's head when the head tracker is mounted on the patient's head. The head cushions 120 can provide support when the patient's head moves sideways. The right head cushion 120a is coupled to the right arm 110a and the left head cushion 120b is coupled to the left arm 110b. More specifically, the head cushions 120 can be coupled to the distal arms 114 of the side arms 110, as shown in FIGS. 2 and 3.

Again, FIGS. 1 to 7 are provided for illustration purposes and other configurations are possible. For example, fewer or more head cushions can be provided. In at least one embodiment, a head tracker may not include any head cushions. In at least another embodiment, a head tracker can include a single head cushion extends between, or spans, both side arms 110. Furthermore, while head cushions 120 are shown as being coupled to the distal portions 114 of the side arms 110, the one or more head cushions can be coupled to the proximal portions 112 of the side arms 110.

Figure 4A:
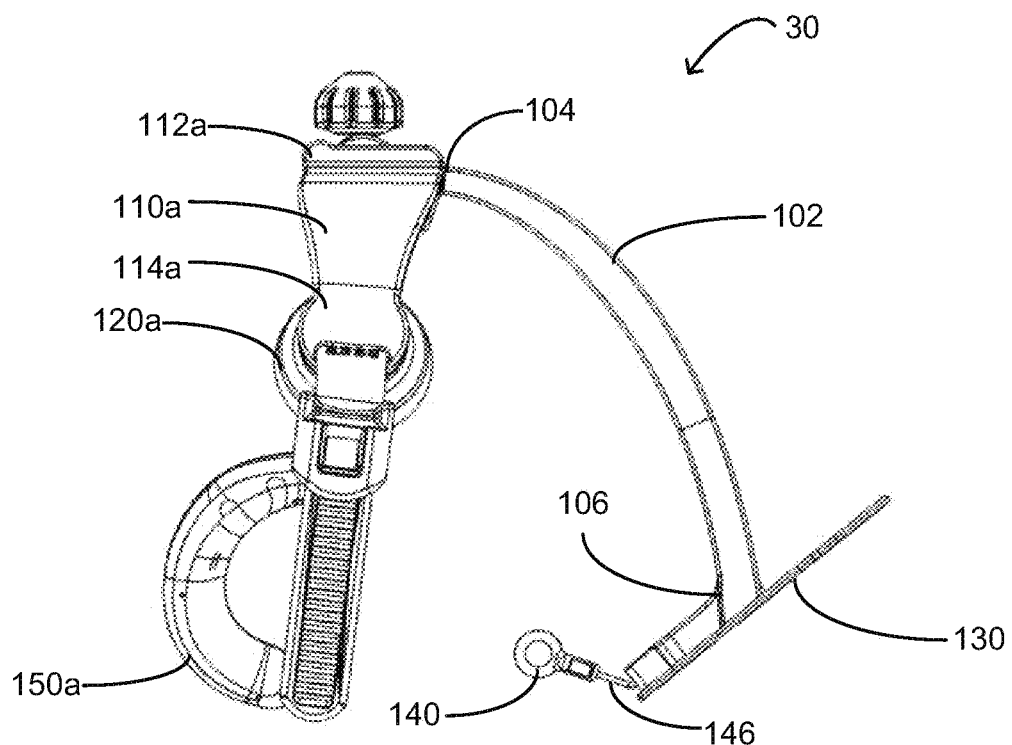
FIG. 4A is an example illustration of a right side view of the head tracker of FIG. 2.
Figure 4B:
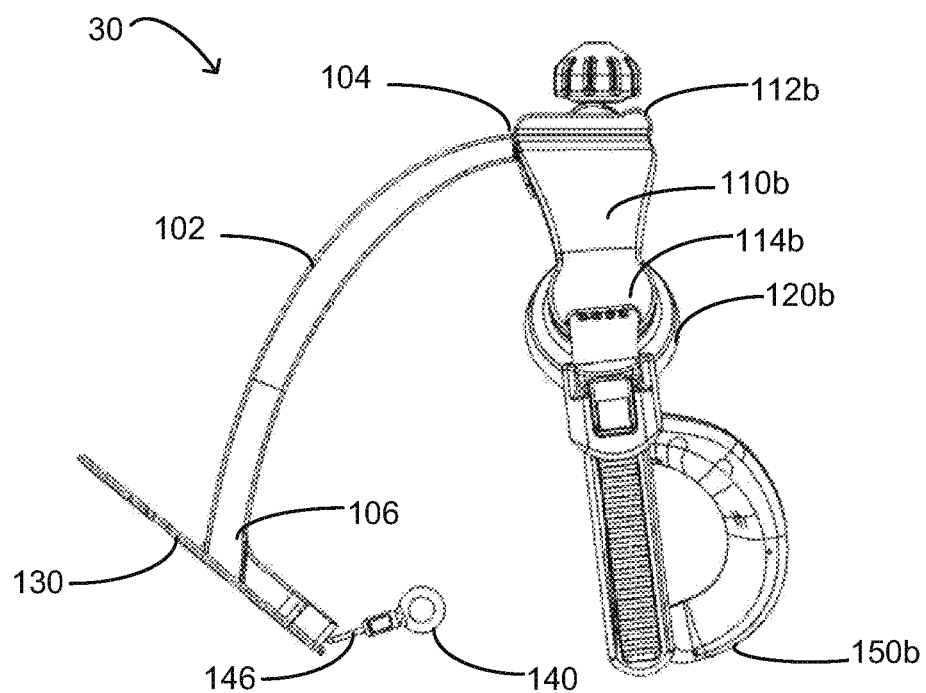
FIG. 4B is an example illustration of a left side view of the head tracker of FIG. 2.

Referring now to FIGS. 4A and 4B, shown therein are example illustrations of a right side view and a left side view of the head tracker 30, according to at least one embodiment. As shown in FIGS. 4A and 4B, the front arm 102 can be configured to extend forwardly from the side arms 110. The forward extension of the front arm 102 from the side arms 110 provides spacing to accommodate the depth of a patient's head from the patient's ears to the patient's face, and in particular, the patient's nose.

As shown in FIGS. 4A and 4B, the nose pad 140 can be coupled to a rear side of the distal portion 106 of the front arm 102. Furthermore, the nose pad 140 can be coupled to the front arm 102 via a nose pad attachment member 146. When the nose pad attachment member 146 is coupled to the rear side of the distal portion 106 of the front arm 102, the nose pad attachment member 146 can extend rearwardly from the rear side of the front arm 102 to allow the nose pad 140 to engage with the nasion region of the patient.

Figure 5:
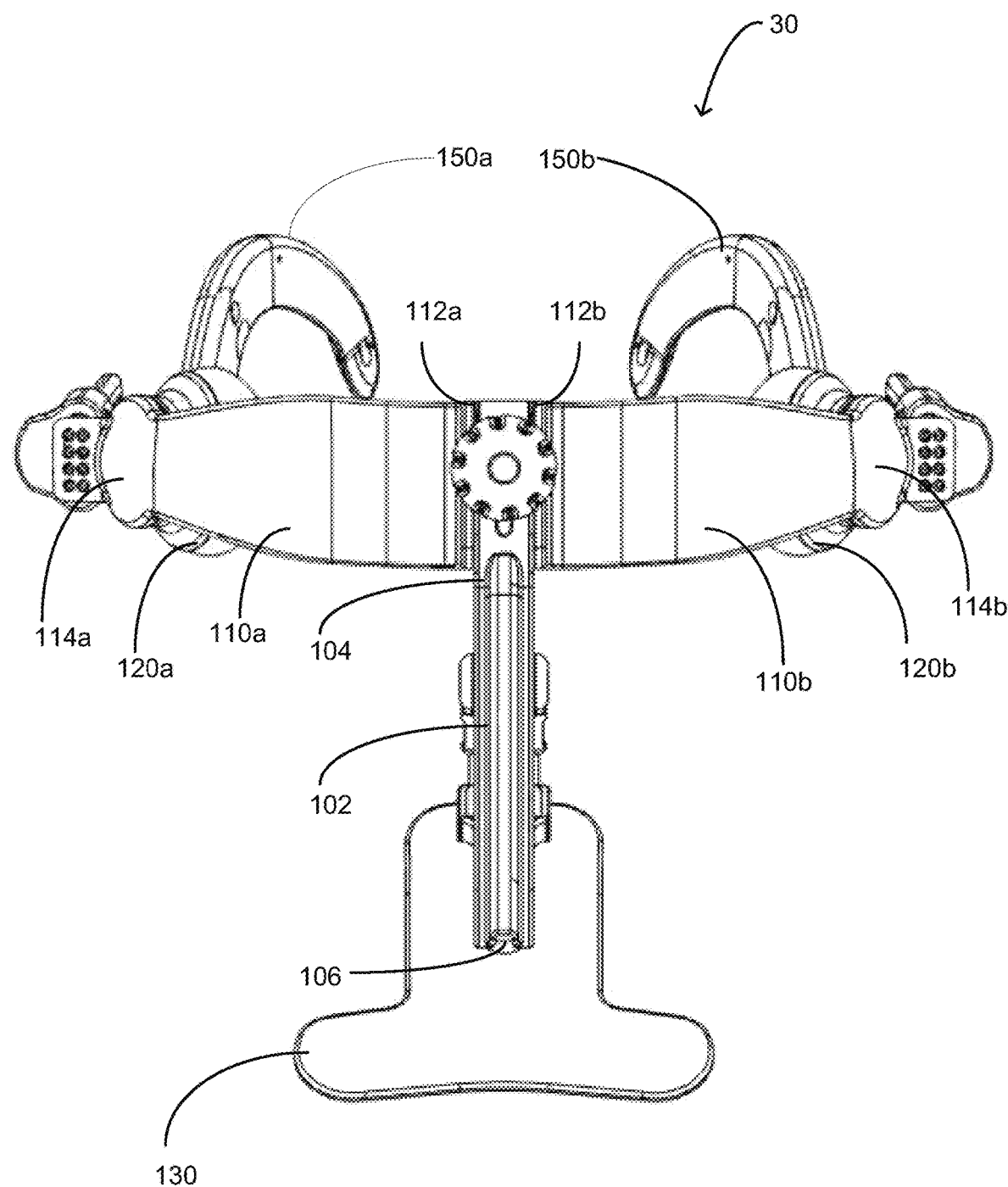
FIG. 5 is an example illustration of a top view of the head tracker of FIG. 2.
Figure 6:
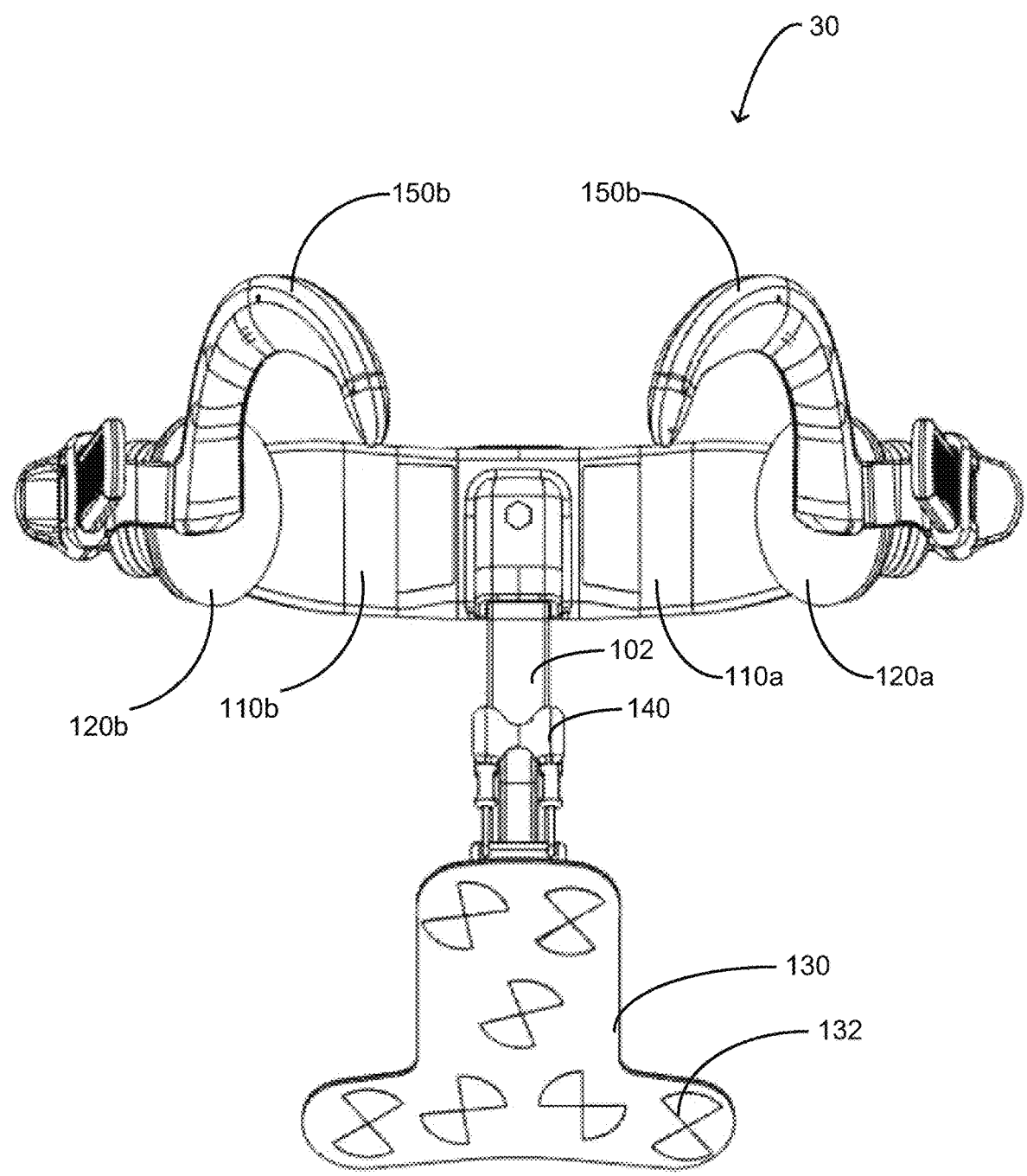
FIG. 6 is an example illustration of a bottom view of the head tracker of FIG. 2.

Referring now to FIGS. 5 and 6, shown therein are example illustrations of a top view and a bottom view of the head tracker 30, according to at least one embodiment. As shown in FIGS. 5 and 6, the two side arms 110 can extend from the coupling portion at substantially opposite directions. For example, the distal portions 114 of the side arms 110 can extend at an angle of approximately 180 degrees from each other.

In addition, the front arm 102 can be substantially perpendicular to each of the side arms 110. For example, the distal portion 106 of the front arm 102 can extend at an angle of about 90 degrees from the distal portion 114a of the right side arm 110a and about 90 degrees from the distal portion 114b of the left side arm 110b.

When the front arm 102 is substantially perpendicular to the side arms 110, the front arm 102 can overlay the middle region of the patient's face, in between the patient's eyes and eyebrow. Moreover, the front arm 102 does not overlay any one of the patient's eyes, eyebrows, and temples when the head tracker 30 is mounted on the patient's head. By not overlaying or covering these areas of the patient's face, the frame 100, including the front arm 102, can be configured to allow for unimpeded or unobstructed hand and arm movements by a user (i.e., surgeon, dentist,) who may be seated behind the patient's head during dental surgery. In particular, the frame 100 can be configured to allow for unimpeded hand and arm movements around the patient's cheeks and temples when accessing the oral cavity.

Figure 7:
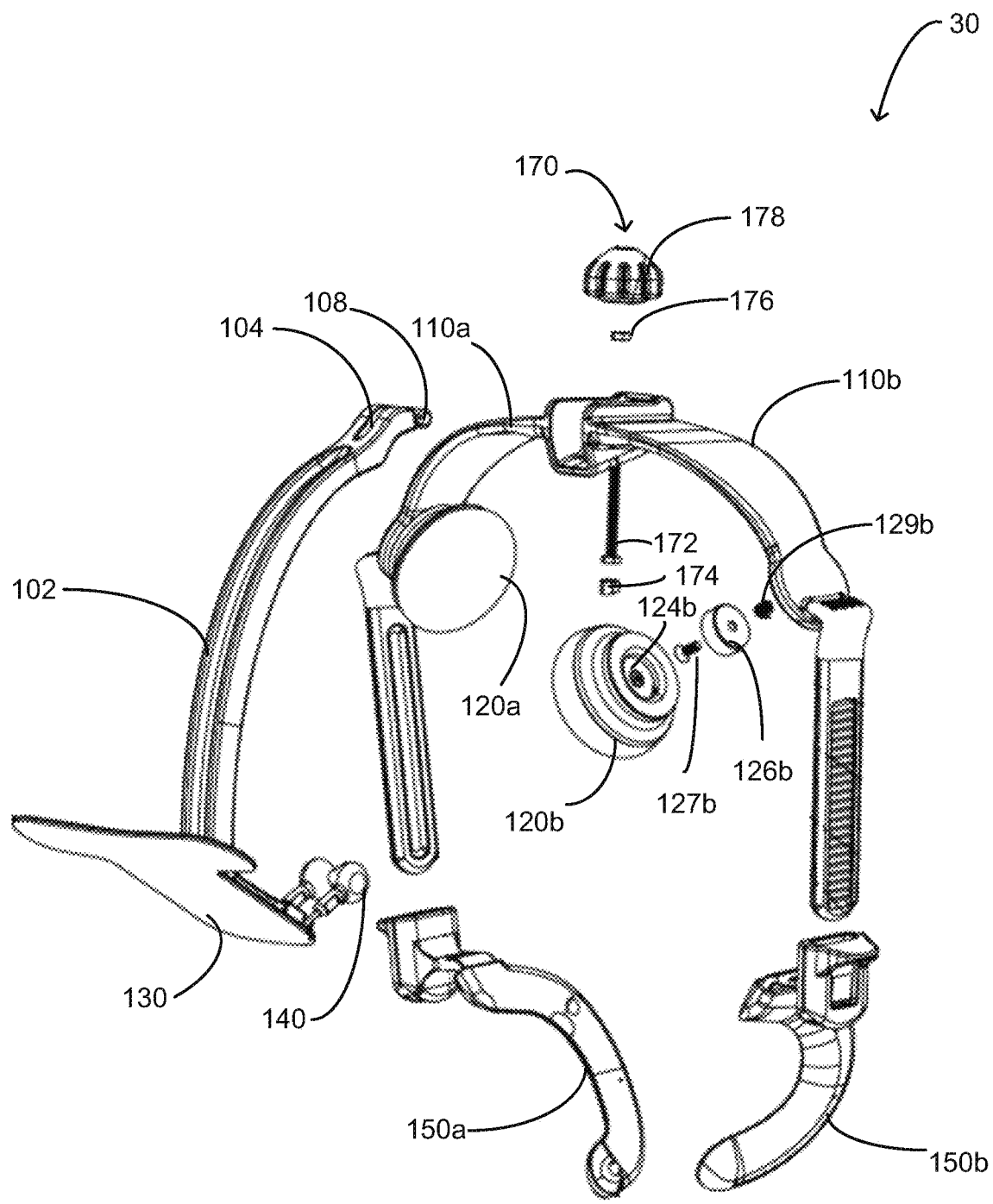
FIG. 7 is an example illustration of an exploded view of the head tracker of FIG. 2.

Referring now to FIG. 7, shown therein is an example illustration of an exploded view of the head tracker 30, according to at least one embodiment. It should be noted that the high contrast optical markings 132 are not shown on the trackable target 130 in FIG. 7.

In at least one embodiment, the frame 100 can include an adjusting mechanism for adjusting a pose of the front arm 102 relative to the two side arms 110. As shown in FIG. 7, the adjusting mechanism 170 of the frame 100 is located at the coupling portion of the frame 100. As a result, the adjusting mechanism 170 adjusts the pose of the front arm 102 relative to the two side arms 100. However, in other embodiments, the adjusting mechanism 170 may not be located the coupling portion of the frame 100 and may adjust the pose of only a portion of the front arm 102 as opposed to the pose of the entire front arm 102.

With the nose pad 140 coupled to the front arm 102 and the pair of ear coupling members 130 coupled to the side arms 110, adjusting the pose of the front arm 102 varies a distance between the one nose pad 140 and at least one ear coupling member of the pair of ear coupling members 130. Varying the distance between the one nose pad 140 and at least one ear coupling member of the pair of ear coupling members 130 provides spacing to accommodate the depth of a patient's head from the patient's ears to the patient's face, and in particular, the patient's nose.

As shown in FIG. 7, in at least one embodiment, the adjusting mechanism 170 can include a threaded bolt or screw 172, nuts 174, 176, and a knob 178. The bolt 172 can pass through the nut 174, the front arm 102, the two side arms 110, and the nut 176. Thus, the adjusting mechanism 170 can couple the front arm 102 and the two side arms 110. The knob 178 can be used to turn the bolt 172, thereby tighten or loosening the coupling between the side arms 110 and the front arm 102 and adjusting the pose of the front arm 102 relative to the two side arms 110. Again, FIGS. 1 to 7 are provided for illustration purposes and other configurations are possible. For example, other adjusting mechanisms 170 are possible. In at least one embodiment, the adjusting mechanism 170 may not include a threaded bolt 172, nuts 174, 176, and/or knob 178.

In at least one embodiment, the frame 100 can include a hinge 108 for coupling the front arm 102 to the frame 100. As shown in FIG. 7, the hinge 108 of frame 100 is located at the coupling portion of the frame 100. As a result, the rotation of the hinge 108 results in rotation of the front arm 102 relative to the two side arms 110. However, in other embodiments, the hinge 108 may not be located at the coupling portion of the frame 100 and may rotate only a portion of the front arm 102 relative to the two side arms 110 as opposed to the entire front arm 102.

With the nose pad 140 coupled to the front arm 102 and the pair of ear coupling members 130 coupled to the side arms 110, rotation of the front arm 102 around the hinge 108 varies a distance between the one nose pad 140 and at least one ear coupling member of the pair of ear coupling members 130. Varying the distance between the one nose pad 140 and at least one ear coupling member of the pair of ear coupling members 130 provides spacing to accommodate the depth of a patient's head from the patient's ears to the patient's face, and in particular, the patient's nose.

In other embodiments, the frame 100 may not include a hinge 108 for coupling the front arm 102 to the frame 100. Instead, the frame 100 can include a slider for coupling the front arm 102 to the frame 100. With a slider, the front arm 102 can slide in forward or backward directions relative to the two side arms 110. With a slider, the adjusting mechanism 170 can be configured to adjust the translation of the front arm 102 within the slider and relative to the two side arms 110.

As shown in FIG. 7, the ear coupling members 150 can be substantially hook shaped for engaging with the back surface of the ears of the patient. In other embodiments, the ear coupling members 150 may not have hook shape and may engage with only a portion of the back surface of the ears of the patient.

In at least one embodiment, the right and left head cushions 120a, 120b can be magnetically coupled to the frame 100. For example, as shown in FIG. 7, a magnet 126b can be coupled to the frame 100 on the left side arm 110b using a bolt 127b and a nut 129b. The left head cushion 120b can include a metal plate 124b for coupling the left head cushion 120b to the magnet 126b. The right head cushion 120a can be similarly magnetically coupled to the frame 100. Magnetically attaching the head cushions 120 allows for easy replacement, substitution, or removal if a different size is needed, or if the head cushions 120 become damaged or dirty.

Figure 8:
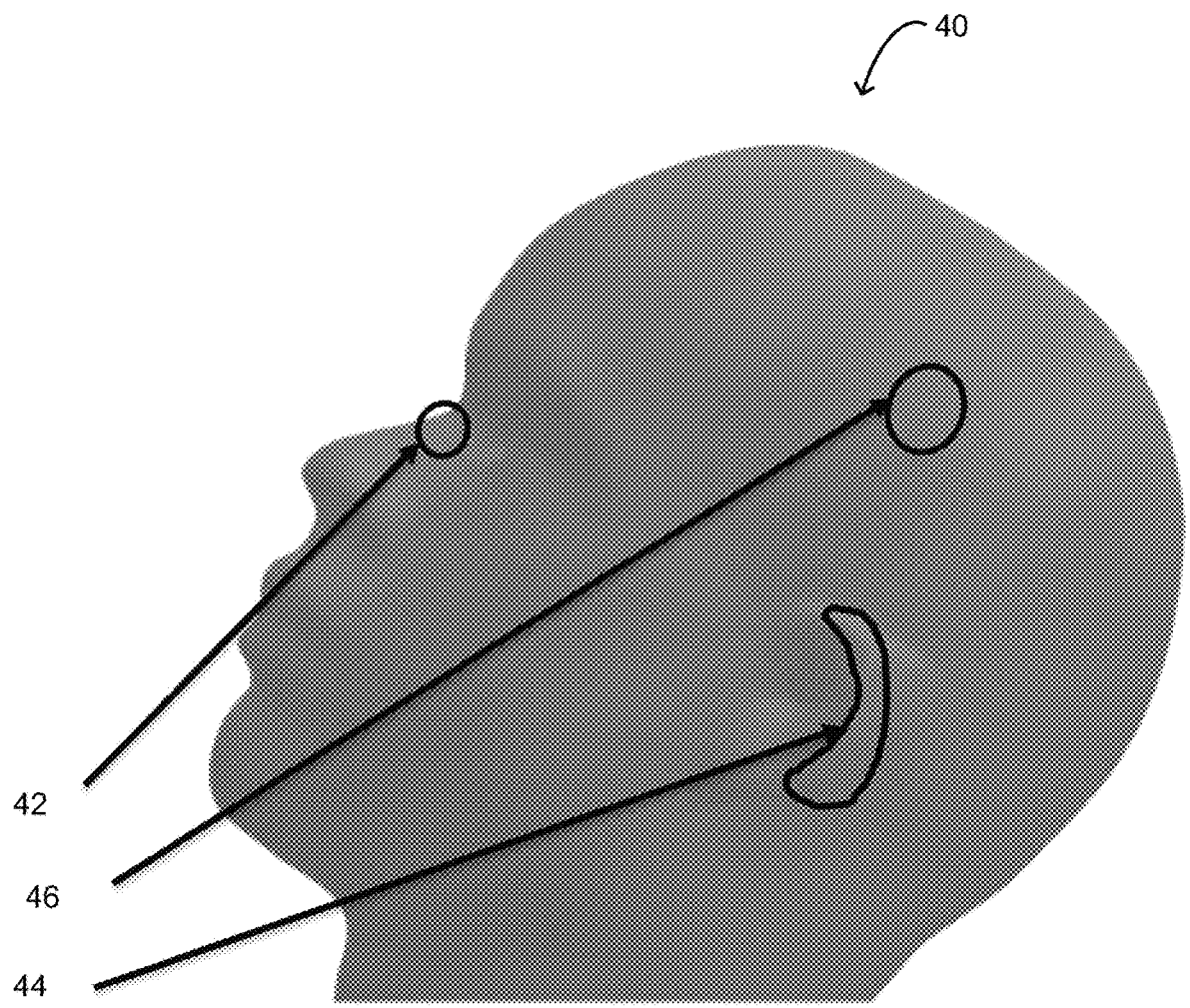
FIG. 8 is an example illustration of contact surfaces of the patient's head with the head tracker of FIG. 2.

Referring now to FIG. 8, shown therein is an example illustration of contact surfaces of the patient's head 40 with the head tracker 30, according to at least one embodiment. When the head tracker 30 is mounted on the head 40 of the patient, the head tracker 30 can engage with three contact surfaces of each of the two sides of the patient's head 40. That is, the head tracker 30 can engage with six contact surface of the patient's head 40: (i) and (ii) the at least one nose pad 140 can engage opposing sides 42 of the nasion region; (iii) and (iv) the ear coupling members 150 can engage with the back surfaces 44 of the ear of the patient; and (v) and (vi) the head cushions 120 can engage with at least a portion 46 of the patient's head. Although the contact surfaces 42, 44, and 46 of only the left side of the patient's head 40 is shown in FIG. 8, it will be understood that the head tracker 30 engages with similar contact surfaces on the right side of the patient's head.

When the head tracker 30 is mounted on the head 40 of the patient, the at least one nose pad contact surface 142 is held against the nasion region 42 and the pair of adjustable ear coupling members 150 are held against the back surfaces 44 of the ears of the patient. In particular, the at least one nose pad contact surface 142 can be held against opposing sides of the nasion region 42. Furthermore, the head tracker 30 can be configured to apply a clamping force to pull the at least one nose pad rearwardly to hold the at least one nose pad contact surface 142 against the nasion region 42 and to pull the pair of adjustable ear coupling members 150 forwardly to hold the pair of adjustable ear coupling members 150 against the back surfaces 44 of the ears of the patient. In at least one embodiment, the frame 100, including the front arm 102 and/or the two side arms 110, the at least one nose pad 140, and/or the pair of adjustable ear coupling members 150 can include biasing components to provide the clamping force.

The clamping force can pull the nose pad 140 against the patient's nasion 42 and the ear coupling members 150 against the back surface of the ears 44. This design can provide a coupling between the frame 100 and the patient's head 40 to resist relative movement between the frame 100 and the patient's head 40 that would otherwise occur from contraction of the patient's facial muscles, movement of the patient's lower jaw, movement of the patient's head relative to the head rest holding it, or an unintentional contact with the frame 100. As a result, the at least one trackable target 130 can be held in a stable spatial relationship with the location of interest in the head 40 of the patient for the duration of the surgery.

In at least one embodiment, the frame 100, including the front arm 102 and/or the two side arms 110, the at least one nose pad 140, and/or the pair of adjustable ear coupling members 150 can be formed of a material having sufficient elasticity to serve as the biasing components configured to hold the at least one nose pad contact surface 142 against the nasion region 42 and to hold the pair of adjustable ear coupling members 150 against the back surfaces 44 of the ears of the patient.

In at least another embodiment, the frame 100, including the front arm 102 and/or the two side arms 110, the at least one nose pad 140, and/or the pair of adjustable ear coupling members 150 can include one or more additional components configured to serve as the biasing components for holding the at least one nose pad contact surface 142 against the nasion region 42 and to hold the pair of adjustable ear coupling members 150 against the back surfaces 44 of the ears of the patient.

Furthermore, the patient's anatomy (e.g., cartilage inside the ears and soft tissue under the nasion region) also provides elasticity to help hold the at least one nose pad contact surface 142 against the nasion region 42 and to hold the pair of adjustable ear coupling members 150 against the back surfaces 44 of the ears of the patient.

In at least one embodiment, the clamping force applied by the head tracker 30 can be configurable to apply a rearward force against the nasion region 42 of the patient that does not cause discomfort for the patient when the head tracker is mounted on the patient's head 40. For example, a rearward force against the nasion region 42 in the range of about 1 to 4 Newtons generally does not cause discomfort for a typical adult patient and is sufficient to hold the frame in a stable spatial relationship with a location of interest in the head 40 of the patient for the duration of the surgery.

Furthermore, the configuration of the head tracker 30 to apply a rearward force can depend on the dimensions of the patient's head 40. Constructing side arms 110 and adjustable ear coupling members 150 of an elastic material, such as nylon or polycarbonate plastic, enables the lateral distance between adjustable ear coupling members 150 to vary to accommodate a wide range of head widths and ear shapes without the need for manual adjustment. By adjusting the vertical distances between the adjustable ear coupling members 150 and the top of the frame 100, and by varying the distances between the nose pad 140 and the adjustable ear coupling members 150 using the adjusting mechanism 170, it is possible to configure the frame 100 in this embodiment such that it will apply a rearward force in the range of about 1 to 4 Newtons on the nose pad 140 when the patient's head is between 5th and 95th percentiles in each of width, length, and height dimensions of adult heads.

As described above, the registration process involves determining a coordinate transform for mapping the reference coordinate space associated with the head to the reference coordinate space associated with the image so that the image of the head can be used as a map or visual aid to guide the placement of surgical instruments and implants at locations of interest in the head during surgery.

It is desirable for the head tracker 30 to maintain a stable spatial relationship between the at least one trackable target with the head of the patient so that the alignment between the head and the image of the head remains the same for the duration of the surgery as initially determined during registration. In particular, the alignment between the head and the image of the head may vary by less than a pre-determined threshold for sufficient precision in the surgical context. For example, the pre-determined threshold can be, for example, 2 millimeters, 1 millimeter, or 0.5 millimeters.

Furthermore, it is desirable for the head tracker 30 to maintain the stable spatial relationship, despite movement of the patient's head, changes to the patient's facial expression, including the opening and closing of the patient's mouth, and/or any other events that commonly occur during surgery, including a sudden application of a transient force up to about 5 Newtons on any part of the frame 100 in any direction. Furthermore, the transient force can be applied for up to about 0.5 seconds. Such transient forces can occur as a result of accidental or inadvertent bumping of the frame 100 by an object, including the user's hand/or arm.

If the at least one trackable target 130 moves relative to the head 40 between the time that the spatial relationship is initially determined (i.e., from registration) and the time that the position of the location of interest is determined (i.e., during surgery), the position of the location of interest determined by the motion tracking system 20 may vary, or be different from, the actual location of interest in the head 40 of the patient. As described above, the spatial relationship may change due to, for example, movement of the patient's lower jaw, changes in the patient's facial expression, and/or movement of the patient's head 40 relative to the head support provided by a dental chair.

However, with head tracker 30, at least one of the at least one nose pad 140 and the pair of adjustable ear coupling members 150 are adjustable to engage with the nasion region 42 of the patient and the back surfaces of the ears of the patient, respectively, when mounted on the patient's head 40. The nasion region 42 and the back surfaces 44 of the ears are desirable contact surfaces of the patient's head 40 because they generally do not move as a result of movement of the patient's jaw. Furthermore, there is little to no underlying muscles at these contact surfaces to cause the frame 100 to move relative to the upper jaw as a result of changes in the patient's facial expression. For example, by engaging with the nasion region 42 which has very little underlying muscle, the nose pad 140 is generally engaged with the nose bone.

Thus, the clamping force applied by the head tracker 30 can be adjustable such that a distance between the position of the location of interest determined by the motion tracking system 20 and the actual location of interest in the head 40 varies by less than 1 millimeter when the head tracker is mounted on the patient's head 40 and the patient's facial expression changes and/or the patient's mouth moves.

When the head tracker 30 is mounted on the patient's head 40, the spatial relationship may also change due to, for example, a sudden application of a transient pressure or force on any part of the frame 100 in any direction. That is, the spatial relationship between the at least one trackable target 130 and the location of interest in the head 40 of the patient may change when the frame 100 is subjected to the application and immediate removal of an external force.

However, the at least one of the at least one nose pad 140, the pair of adjustable ear coupling members 150, and the frame 100, including the biasing components, can be configured to deflect such transient forces. More specifically, the head tracker 30 can be configured to restore the stable spatial relationship when the frame 100 is subjected to a transient force on any part of the frame 100. For example, the external transient force can be applied for less than about 0.5 second and/or have a magnitude of up to about 5 Newtons.

Thus, the clamping force applied by the head tracker 30 can be adjustable such that a distance between the position of the location of interest determined by the motion tracking system 20 and the actual location of interest in the head 40 varies by less than 1 millimeter following the application and immediate removal of a transient force.

Referring now to FIG. 9A, shown therein is an example illustration of at least one nose pad 140 of the head tracker 30. The nose pad 140 defines nose pad contact surfaces 142 for engaging with the nasion region 42 of the patient when the head tracker 30 is mounted on the patient's head 40. In particular, the nose pad 140 defines nose pad contact surface 142 for engaging with two opposing sides of the nasion region 42.

The nose pad 140 can also include a first insert 144a and a second insert 144b (herein collectively referred to as inserts 144) for coupling the nose pad 140 to the nose pad attachment member 146. In at least one embodiment, the nose pad 140 can be coupled directly to the nose pad attachment member 146 without inserts 144.

As shown in FIGS. 4A and 4B, the nose pad attachment member 146 can couple the nose pad 140 to the front arm 102 of the head tracker 30. In at least one embodiment, the nose pad attachment member 146 can be coupled to the front arm 102 via the at least one trackable target 130. That is, the nose pad attachment member 146 can be coupled to the at least one trackable target 130, which in turn, is coupled to the front arm 102 of the head tracker 30.

In at least one embodiment, the nose pad 140 can be adjustably coupled to the frame 100. For example, the nose pad attachment member 146 can be pliable, allowing the coupling of the nose pad 140 to the frame 100 to be adjusted to accommodate variations in the shape of the nasion region 42 in patients. In at least one embodiment, the nose pad attachment member 146 can be made of a metal wire, such as annealed stainless steel.

In at least one embodiment, the at least one nose pad 140 can be detachably coupled to the frame 100. That is, the at least one nose pad 140 can be detached from the frame to allow for easy replacement, substitution, or removal if a different size is needed, or if the nose pad 140 becomes damaged or dirty.

As shown in FIG. 9A, the nose pad 140 can include a bridge portion 148 that is coupled to each of the two nose pad contact surface area locations 142a, 142b. The bridge portion 148 can further engage with a bridge of the patient's nose.

In at least another embodiment, the nose pad 140 may not include a bridge portion 148 and may include two adjustable nose pads. With two adjustable nose pads, the orientation of each of the two nose pads can be independently adjustable relative to the frame 100. In at least one embodiment, the orientation of each of the two nose pad contact surface area locations 142 can be securable relative to the frame 100. That is, after adjusting the orientation of the nose pad contact surface area locations 142 relative to the frame 100, the orientation can be locked or fixed.

The nose pad contact surfaces 142 of the nose pad 140 can be deformable to match the shape of the nasion region 42 of the patient. The nose pad contact surfaces 142 can deform to define actual nose pad contact surface area locations. The actual nose pad contact surface area locations can contact the actual nasion region 42 of the patient. As shown in FIG. 9A, the actual nose pad contact surface area locations can contact two opposing sides of the actual nasion region 42.

In at least one embodiment, the nose pad 140 can be made of a soft material. For example, the nose pad contact surface 142 can be made of silicone rubber. A nose pad made of a soft material can improve comfort for the patient, as well as absorb minor skin movements.

Referring now to FIG. 9B, shown therein is an example illustration of a left adjustable ear coupling member 150*b* of the head tracker 30. Although only the left adjustable ear coupling member 150*b* is shown in FIG. 9B, it will be understood that the right adjustable ear coupling member 150*a* of the head tracker 30 can have similar features.

The ear coupling member 150*b* can include an ear frame 152*b* having an upper portion and a lower portion. The lower portion of the ear frame 152*b* is encased with a cover 154*b* to provide a padding. The cover 154*b* can be made of silicone rubber or a similar soft durable rubber. The silicone rubber padding can define at least one ear coupling contact surface for engaging with the at least a portion of a back surface 44 of the ear of the patient. The ear coupling member 150*b* having a cover 154*b* made of a soft material such as silicone rubber cover 154*b* can improve comfort for the patient, as well as absorb minor skin movements.

In at least one embodiment, the ear frame 152*b* can include an inwardly extending members 153*b* for coupling the ear coupling member 150*b* to the side arm 110*b*. The pair of ear coupling members 150 can be spaced apart to accommodate the width of the patient's head 40 therein between the ear coupling members 150. Accordingly, a pair of inwardly extending members 153 (e.g., a right inwardly extending member 153*a* and the left inwardly extending member 153*b*) can position the pair of ear coupling members 150 to be spaced closer to one another than the side arms 110 are spaced to one another, while still accommodating the width of a patient's head 40 between the pair of ear coupling members. The inwardly extending members 153 can help ensure that there is no contact between the frame 100 and the skin about the ears, since such contact may prevent the ear coupling members 150 from snugly fitting into the valley behind the ears. A loose fit may lead to patient discomfort and reduced stability of the coupling between the frame 100 and the patient's head 40.

The upper portion of the ear frame 152*b* has a receiver 156*b*. The receiver 156*b* has a recess 158*b* and a tab 160*b*. The receiver 156*b* can receive a portion of the left side arm 110*b* through the recess 158*b* for detachably coupling the adjustable ear coupling member 150*b* to the side arm 110*b*. Detachably coupling the adjustable ear coupling member 150*b* to the side arm 110*b* via the receiver 156*b* allows for easy replacement, substitution, or removal if a different size is needed, or if the adjustable ear coupling member 150*b* become damaged or dirty.

Referring now to FIG. 9C, shown therein is an example illustration of the left adjustable ear coupling member 150*b* coupled to the left side arm 110*b* of the head tracker 30. Although only the left adjustable ear coupling member 150*b* and the left side arm 110*b* are shown in FIG. 9C, it will be understood that the right adjustable ear coupling member 150*a* can be similarly coupled to the right side arm 110*a* as the left adjustable ear coupling member 150*b* is coupled to the left side arm 110*b* of the head tracker 30.

In at least one embodiment, each of the side arms 110 can include a slider 162*a*, 162*b* (herein collectively referred to as sliders 162) coupled to the distal portions 114 of the respective side arms 110. The slider 162*b* can be coupled to the distal portion 114*b* of the side arm 110*b* via a connector 164*b* on the distal portion 114 of the side arm 110. The slider 162*b* of the side arm 110*b* can be inserted into the receiver 156*b*. The slider 162*b* has a plurality of notches 166*b* for receive the tab 160*b* when the slider 162*b* is inserted into the receiver 156*b* to serve as a detent to keep the slider 162*b* at a desired height.

Inwardly extending members 153 of adjustable ear coupling members 150 can be made of a flexible material to allow the adjustable ear coupling members 150 to rotate outwards to fit a range of orientations of the valleys behind the patient's ears, while maintaining a mild inward force towards the patient's head 40 to ensure that the forward force applied to the ear coupling members 150 does not cause the ears to fold forward.

The tab 160*b* can move into one of the plurality of notches 166*b*, preventing upward motion of the slider 162*b*. A user can pull the slider 162*b* down to a desired height to fit the patient's head 40, and in particular to accommodate the height of the patient's ears relative to the patient's head 40. To change the height of the adjustable ear coupling member 150*b*, a user can push the tab 160*b* to remove the tab 160*b* from one of the notches 166*b*. The slider 162*b* can then freely move up and down within the receiver 156*b*. Thus, the slider 162*b* allows for translational movement of the adjustable ear coupling member 150 in a vertical direction.

Figure 9D:
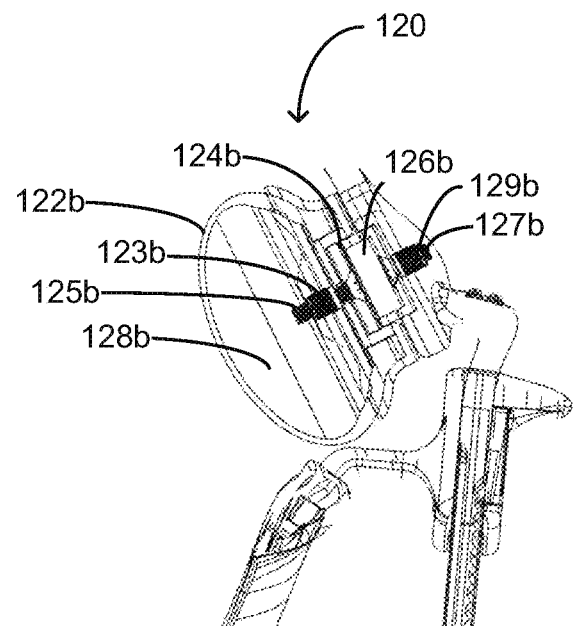
FIG. 9D is an example illustration of a side sectional view of the head cushion of FIG. 9B.

Referring now to FIG. 9D, shown therein is an example illustration of a side sectional view of the head cushion 120*b* of the head tracker 100. Although only the left head cushion 120*b* and the left side arm 110*b* are shown in FIG. 9D, it will be understood that the right head cushion 120*a* can have similar features as the left head cushion 120*b*. Furthermore, the right head cushion 120*a* can be similarly coupled to the right side arm 110*a* of the head tracker 30 as the left head cushion 120*b* is coupled to the left side arm 110*b*.

As described above, the magnet 126*b* can be coupled to the frame 100 using the bolt 127*b* and the nut 129*b*. As shown in FIG. 9D, the metal plate 124*b* can be coupled to the head cushion 120*b* using a bolt 125*b* and a nut 123*b*. Thus, the head cushion 120*b* having a metal plate 124*b* can be magnetically coupled to the frame 100 having magnet 126*b*. Magnetic coupling of the head cushion 120*b* to the frame 100 allows for convenient and repeatable removal and attachment of the head cushion 120*b* to the frame 100.

The left head cushion 120*b* also has a cover 122*b*. The cover 122*b* can be made of a pliable or elastic material such as fabric, leather, faux leather, or rubber. The cover 122*b* can be thin. The cover 122*b* can be filled with a clay-like, plastic, material or substance 128*b* selected to be deformable to enable the head cushion 120*b* to conform, or adapt its surface, to the shape of the of the at least a portion of the patient's head 40 that the head cushion 120*b* engages with during the mounting of the head tracker 30 to the head of a patient. To provide comfort for the patient, the substance 128*b* filling the head cushion 120*b* can be selected to slowly take the shape of the at least a portion of the patient's head 40 by gentle pressure and to not subsequently attempt to resume its original shape, which could cause the adjustable ear coupling members 150 to be lifted up and away from the valley behind the ear.

However, the substance 128*b* filling the head cushion 120*b* can be selected to also resist shape changes due to the sudden application of a transient pressure or force, thereby resisting sudden movement of the frame 100 relative to the head of the patient. That is, the substance 128*b* filling the head cushion 120*b* can resist deformation following the application and immediate removal of a force, for example, when the force is applied for less than about 0.5 second. The head cushion 120*b* may be subjected to such a transient pressure or force as a result of accidental or inadvertent bumping of the frame 100 by an object, including the user's hand/or arm. In at least one embodiment, the substance 128*b* filling the head cushion 120*b* can strongly resist deformation following the application and immediate removal of a force of up to about 5 Newtons on the side arm 110*b* that the head cushion 120*b* is coupled to. Thus, the material 128*b* of the head cushion 120*b* can allow the head cushion 120*b* to adapt to fit the shape of the patient's head and to also help the frame 100 resist displacement due to accidental transient forces. In at least one embodiment, the material filling the head cushions 120 can be a polymer composite such as a lightweight molding clay named Morph™ made by ORB™ and/or other similar lightweight molding clays. In another embodiment, the substance 128*b* filling the head cushion 120*b* can consist of high friction small particles, such as grains of sand.

Figure 9E:
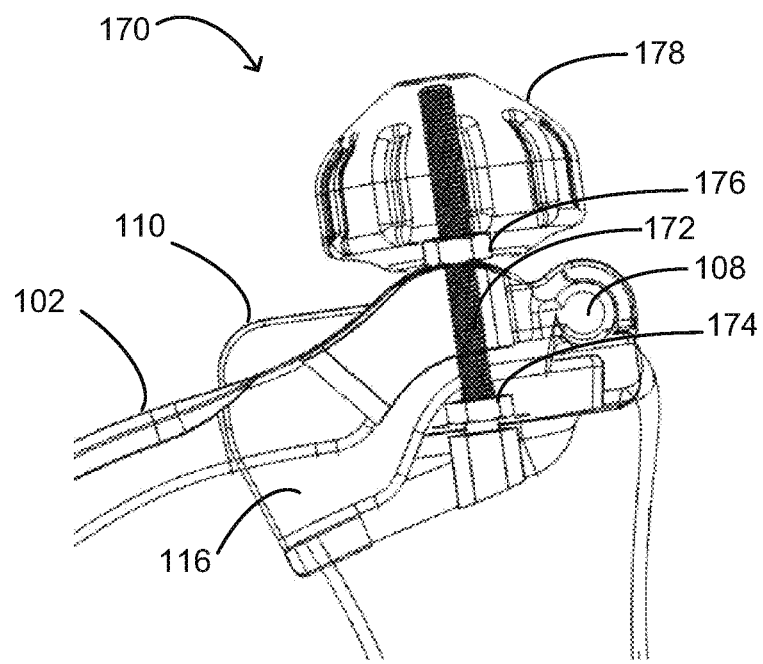
FIG. 9E is an example illustration of an adjusting mechanism and a hinge of the head tracker of FIG. 2.

Referring now to FIG. 9E, shown therein is an example illustration of the adjusting mechanism 170 and the hinge 108 of the head tracker 30. As described above, the hinge 108 couples the front arm 102 to the frame 100 and the adjustable fastener 170 adjusts a pose of the front arm 102 relative to the frame 100, that is, the two side arms 110. The adjusting mechanism 170 includes a threaded bolt 172 with nut 174 coupled to the frame 100. Bolt 172 passes through nut 176, which can be coupled to knob 178 for turning nut 176. As the knob 178 is rotated (e.g., by the patient themselves, surgeon, or dentist, etc. . . . ), nut 176 is lowered, thereby pushing arm 102 to rotate it downwards, or elevated along bolt 172, thereby releasing front arm 102 to rotate upwards, causing the nose pad 140 to move towards or away from the ear coupling members 150.

As shown in FIG. 9E, the side arms 110 can define a receptacle within which the front arm 102 can be positioned. The receptacle can have high side walls 116 to provide side stability for the rotation of the front arm 102 around the hinge 108.

As shown in FIG. 9E, both the adjusting mechanism 170 and the hinge 108 can both be located at the coupling portion of the frame 100. Thus, the adjusting mechanism 170 can be configured to adjust the rotation of the front arm 102 about the hinge 108, that is, the rotation of the front arm 102 relative to the two side arms 110.

The rotation of the front arm 102 relative to the two side arms 110 can be adjusted to accommodate the dimensions of the patient's head 40. For example, the front arm 102 can be adjusted by rotating knob 178 to a position in which the nose pad contact surfaces 142, the adjustable ear coupling members 150, and/or the head cushions 120 comfortably engage with contact regions 42, 44, and 46 on the patient.

When the front arm 102 is in a desired position, the adjusting mechanism 170 can be tightened further to cause the force pulling the nose pad 140 against the nasion region 42 to increase. To ensure the maximal resistance to movement of the frame 100 relative to the patient's head 40 without causing excessive discomfort, the patient can be asked to turn knob 178 by themselves to adjust the clamping force of the frame 100 (i.e., rearward pull on their nasion region 42 and forward pull on the back of their ears 44) to the maximum level that the patient feels is still comfortable for them to tolerate during the subsequent surgery.

Figure 10:
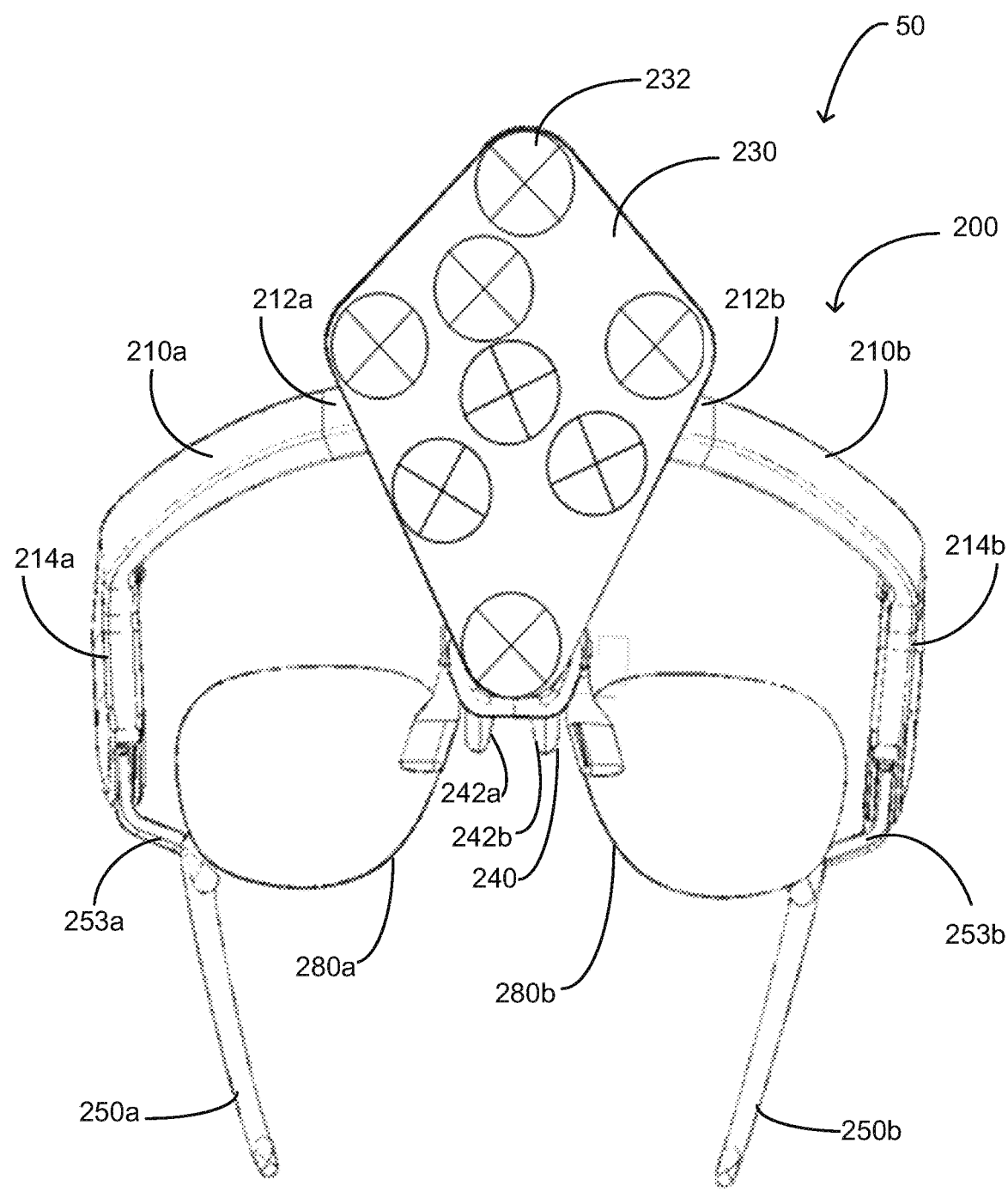
FIG. 10 is example illustration of a front view of another head tracker of the system of FIG. 1, according to at least another embodiment.

Referring now to FIG. 10, shown therein is an example illustration of a front view of another head tracker 50, according to at least one embodiment. Similar to head tracker 30, head tracker 50 can be used in system for tracking a head 40 of a patient, such as system 10 of FIG. 1.

The head tracker 50 includes a frame 200, at least one trackable target 230, at least one nose pad 240, a pair of adjustable ear coupling members 250, and a right lens 280*a* and a left lens 280*b* (herein collectively referred to as a pair of lenses 280). As shown in FIG. 10, the frame 200 does not include head cushions 120. It should be noted that FIG. 10 is provided for illustration purposes and other configurations are possible. For example, in other embodiments, the head tracker may not include the pair of lenses 280, such as head tracker 30. As well, additional trackable targets 230 can be provided.

The frame 200 of the head tracker 50 includes a front arm (not shown in FIG. 10) and two side arms 210 coupled to the front arm. The two side arms 210 include a right arm 210*a* and a left arm 210*b*. Each side arm 210*a*, 210*b* has a proximal portion 212*a*, 212*b* (herein collectively referred to as the proximal portions 212 of the side arms 210) and a distal portion 214*a*, 214*b* (herein collectively referred to as the distal portions 212 of the side arms 210), respectively. Each side arm 210*a*, 210*b* is coupled to the frame 200 at the proximal portion 212*a*, 212*b* of the respective side arm 210*a*, 210*b*. The side arms 210 extend laterally such that the distal portions 214 of the side arms 210 are spaced apart to accommodate a width of a patient's head 40 between the side arms 210.

As described above, the head tracker 50 includes the trackable target 230 coupled to the frame 200. Similar to trackable target 130, the trackable target 230 can include a plate on which the high contrast optical markings 232 are located. The trackable target 230 can be tracked by a motion tracking system, such as motion tracking system 20 of FIG. 1, to determine the position and the orientation of the trackable target 230.

The head tracker 50 also includes a nose pad 240 that defines two nose pad contact surfaces, that is, a right nose pad contact surface 242*a* and a left nose pad contact surface 242*b* (herein collectively referred to as 242) for engaging with of a nasion region 42 of the patient when the head tracker 50 is mounted on the patient's head 40. As shown in FIG. 10, the nose pad 240 defines two nose pad contact surfaces 242 for engaging with two opposing sides of the nasion region 42. The nose pad 240 is be coupled to the frame 200.

Again, FIG. 1 is provided for illustration purposes and other configurations are possible. For example, additional nose pads can be provided. In at least one embodiment, a head tracker can include two nose pads, each nose pad defining a nose pad contact surface for engaging with the nasion region of the patient. In at least one embodiment, a head tracker can include two nose pads, each nose pad defining a nose pad contact surface for engaging one of two opposing sides of the nasion region of the patient.

The head tracker 50 includes a pair of adjustable ear coupling members 250. In particular, the head tracker 50 includes a right adjustable ear coupling member 250*a* and a left adjustable ear coupling member 250*b* (herein collectively referred to as the adjustable ear coupling members 250 or the ear coupling members 250). The adjustable ear coupling members 250 are shaped for engaging with at least a portion of a back surface of an ear of the patient. More specifically, the ear coupling members 250 have a hook shape for engaging with the back surface of the ears of the patient. As shown in FIG. 10, the adjustable ear coupling members 250 can be coupled to the distal portions 214 of the respective side arms 210.

As shown in FIG. 10, the frame 200 includes a left inwardly extending member 253*a* and a right inwardly extending member 253*b* (herein collectively referred to as inwardly extending members 253) for coupling each of the adjustable ear coupling members 250*a*, 250*b* to its respective arm 210a, 210b, and more specifically, the distal portion 214a, 214b of its respective arm. The inwardly extending members 253a, 253b can position the ear coupling members 250a, 250b to be spaced closer to one another than the spacing provided between the side arms 210a, 210b for accommodating the width of the patient's head 40.

As mentioned above, the frame 200 includes a pair of lenses 280 coupled to the frame 200. When the head tracker 50 is mounted on the patient's head 40, the lenses 280 can provide protection to the patient's eyes from light and debris during surgery. In at least one embodiment, the lenses 280 can be tinted. In at least one embodiment, the frame 200 can include a damper (not shown in FIG. 10) for absorbing forces acting on the lenses 280 to reduce transmitted forces to the frame 200. For example, if a user accidentally contacts, or applies force, to one of the lenses 280, the damper can reduce the motion of the frame 200 to maintain the stable spatial relationship between the at least one trackable target 230 and a location of interest in the head 40 of the patient.

Figure 11:
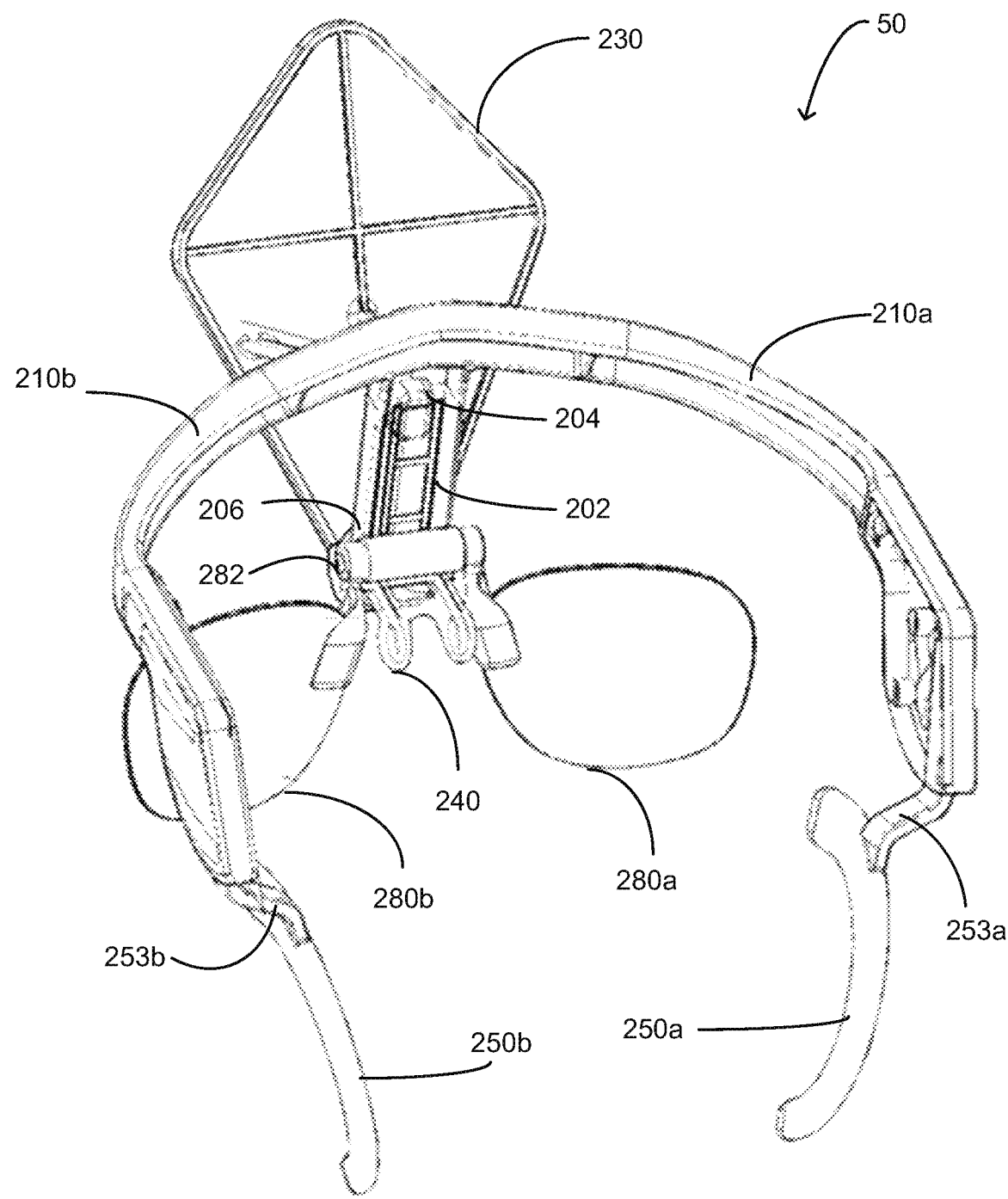
FIG. 11 is an example illustration of a rear perspective view of the head tracker of FIG. 10.

Referring now to FIG. 11, shown therein is an example illustration of a rear perspective view of the head tracker 50 of FIG. 10. As shown in FIG. 11, the front arm 202 can have a proximal portion 204 and a distal portion 206. The front arm 202 is coupled to the frame 200 at the proximal portion 204 of the front arm 202. Since the front arm 202 of head tracker 50 extends downwardly, the proximal portion 204 can also be referred to as an upper portion of the front arm 202 and the distal portion 206 can also be referred to as a lower portion of the front arm 202. The front arm 202 may also be referred to as a front member.

The frame 200 can include a coupling portion for coupling the front arm 202 and the side arms 210. In particular, the coupling portion can include the proximal portion 204 of the front arm 202 and the proximal portions 212 of the side arms 210. The coupling portion can be configured to be located above the top of the patient's forehead when the head tracker 50 is mounted on the patient's head 40. That is, the coupling portion can be configured to overlay the patient's forehead when the head tracker 50 is mounted on the patient's head 40.

Each of the trackable target 230, the nose pad 240, and the lenses 280 can be coupled to the front arm 202 of the frame 200. As shown in FIG. 11, the nose pad 240 can be coupled to the distal portion 206 of the front arm 202. Also shown in FIG. 11, the lenses 280 can be coupled to the distal portion 206 of the front arm 202.

In at least one embodiment, the lenses 280 can be detachably coupled to the frame 200. That is, the lenses can be detached from the frame for easy replacement, substitution, or removal if a different size is needed, or if the lenses 280 become damaged or dirty.

In at least one embodiment, the lenses 280 can be hingeably coupled to the frame 200. For example, lenses 280 can be coupled to the frame 200 by at least one hinge. As shown in FIG. 11, the lenses 280 can be coupled to the frame 200 by hinge 282. The hinge 282 can allow the lenses 280 to be lifted and lowered. Before and after the surgery, such as when the frame 200 is being mounted on the patient's head 40, the lenses 280 can be lifted to reduce interference. During surgery, the lenses 280 can be lowered for protection.

Figure 12:
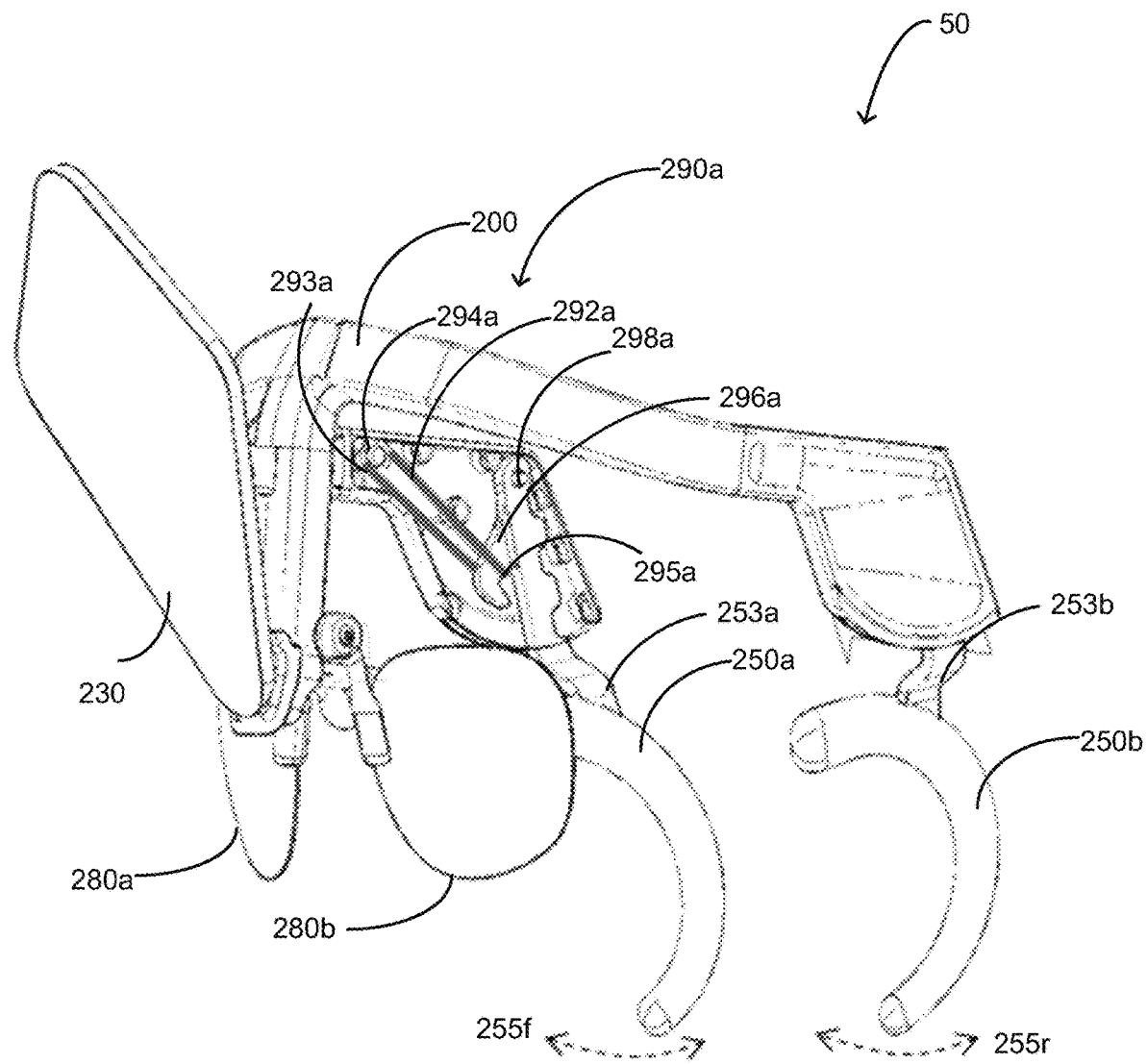
FIG. 12 is an example illustration of a front perspective view of the head tracker of FIG. 10.

Referring now to FIG. 12, shown therein is an example illustration of a front perspective view of the head tracker 50 of FIG. 10. It should be noted that the high contrast optical markings 232 are not shown on the trackable target 230 in FIG. 12.

The frame 200 also includes biasing components for providing a clamping force to pull the at least one nose pad 240 rearwardly and to pull the pair of adjustable ear coupling members 250 forwardly. By pulling the at least one nose pad 240 rearwardly, the nose pad 240 is held against the nasion 42. By pulling the ear coupling members 250a forwardly, the adjustable ear coupling members 250 are held against the back of the ears 46. As a result, the clamping force holds the at least one trackable target in a stable spatial relationship with the location of interest in the head 40 of the patient.

As shown in FIG. 12, the head tracker 50 can also include a biasing mechanism 290a to provide the clamping force for coupling the frame 200 and the patient's head 40 to resist attempts to move the frame 200 or the patient's head 40 relative to the other when the patient's facial muscles contract, the patient's lower jaw moves, the patient's head 40 moves relative to the head rest upon which the head 40 is positioned, or unintentional contact. The biasing mechanism 290a of the right side arm 210a of the head tracker 50 include a biasing member 292a, an anchor member 294a, a hinge 298a, and a hook 296a. A similar biasing mechanism can be provided for the left side arm 210b of the head tracker 50. In at least one embodiment, the biasing member 292a can be at least one of an elastic member and a spring member. In at least one embodiment, the biasing member 292 can be a spring member having an adjustable force.

The biasing member 292a can have a stationary end 293a and an extendable end 295a that is opposed to the stationary end 293a. The stationary end 293a of the biasing member 292a can be coupled to the right side arm 210a and an extendable end 295a of the biasing member 292a can be coupled to the right adjustable ear coupling member 250a. More specifically, the stationary end 293a of the biasing member 292a can be coupled to the anchor member 294a that is attached to the right side arm 210a. The anchors 294a can receive the stationary end 293a of the biasing member 292a.

The hinge or pivot member 298a can be used for coupling the adjustable ear coupling member 250a to its respective side arm 210a. In at least one embodiment, the hinge 298a allows the ear coupling member 250a to be adjustable. The adjustable ear coupling member 250a can rotate, or pivot around the hinge 298a, thereby adjusting the position of the adjustable ear coupling member 250a relative to the side arm 210a. More specifically, the adjustable ear coupling member 250a can pivot forward and backward relative to the side arm 210a.

As shown in FIG. 12, the adjustable ear coupling member 250a can include the hook 296a. The hook 296a can engage the extendable end 295a of the biasing member 292a. The extendable end 295a of the biasing member 292a can be coupled to the hook 296a. When the adjustable ear coupling member 250a rotates around the hinge 298a, the hook 296a also rotates, adjusting the distance between the stationary end 293a and the extendable end 295a. When the adjustable ear coupling member 250a rotates in a rearward direction 255r, the hook 296a pulls the extendable end 295a of the biasing member 292a to lengthen the biasing member 292a. Lengthening the biasing member 292a further pulls the at least one nose pad rearwardly and the pair of adjustable ear coupling members forwardly. When the adjustable ear coupling member 250a rotates in a forward direction 255f, the hook 296a releases the extendable end 295a of the biasing member 292a to shorten the biasing member 292a. Shortening the biasing member 292a releases the force that pulls the at least one nose pad rearwardly and the pair of adjustable ear coupling members forwardly.

The biasing member 292a extends between the anchor 294a and the hook 296a. The biasing member 292a apply a torque to the ear coupling member 250a to turn them around the hinge 298a to bias them forwards. When putting the frame 200 on the patient, a user can pull the ear coupling member 250a to the rear of the frame 200 and place the frame 200 on the patient. The biasing member 292a can then pull the respective ear coupling members 250a forward against the ears of the patient, thereby securing the head tracker 30 on the head 40 of the patient. That is, the biasing components of head tracker 50 can provide a biasing mechanism 290a for providing a clamping force that biases a position of the ear coupling members 250 toward the front arm 202.

Figure 13:
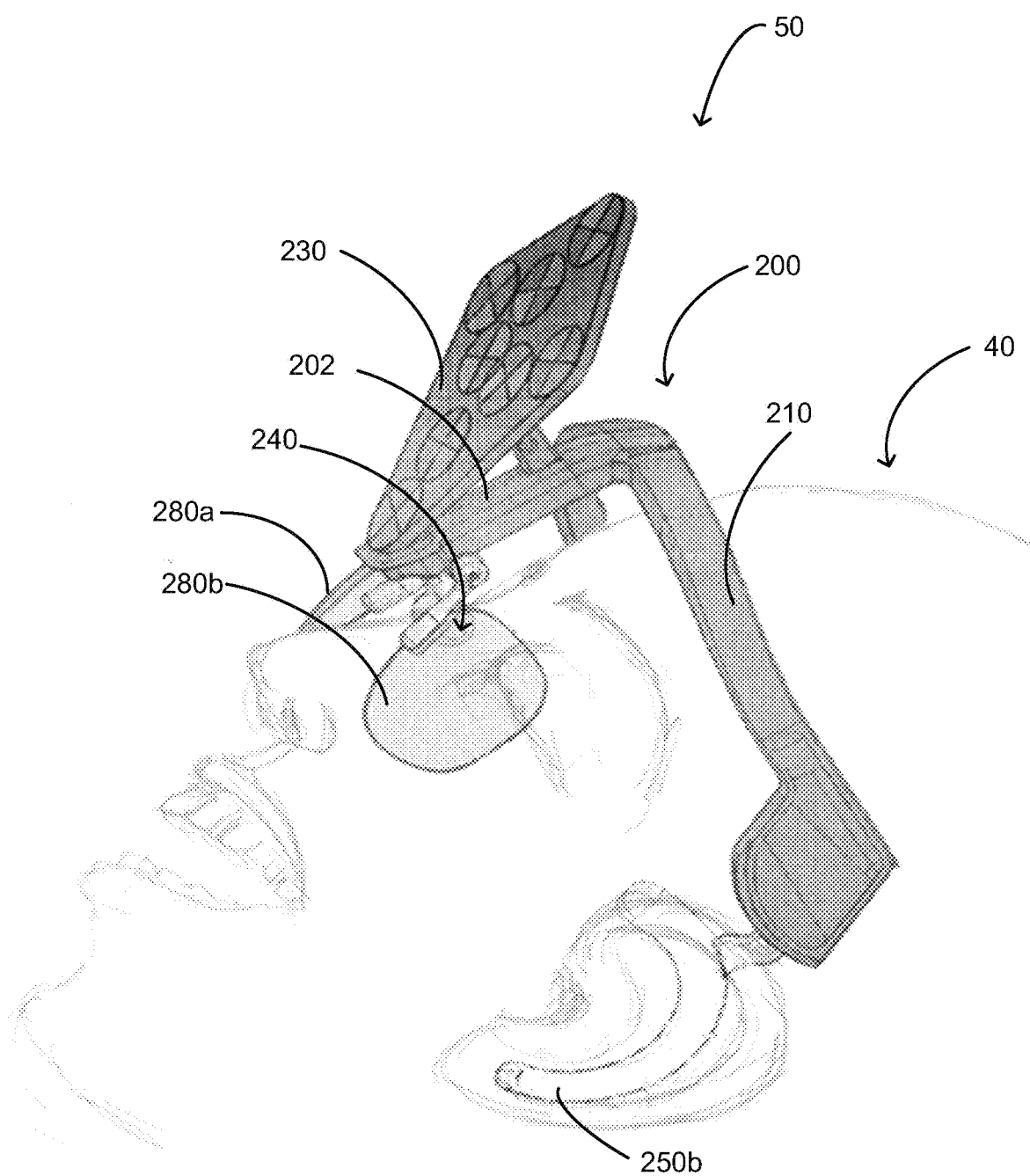
FIG. 13 is an example illustration of the head tracker of FIG. 10 mounted on a patient's head.

Referring now to FIG. 13, shown therein is an example illustration of the head tracker of FIG. 10 mounted on the patient's head 40. As described above, the coupling portion of frame 200 can be configured to be located above the top of the patient's forehead when the head tracker 50 is mounted on the patient's head 40, as shown in FIG. 13.

As well, the front arm 202 is substantially perpendicular to the side arms 210. The front arm 202 can overlay the middle region of the patient's face, in between the patient's eyes and eyebrow. Moreover, the front arm 202 does not overlay any one of the patient's eyes and eyebrows when the head tracker 50 is mounted on the patient's head 40.

It should be noted that FIGS. 10 to 13 are provided for illustration purposes and other configurations are possible. For example, other configurations for the frame 200 to not overlay the patient's eyes, eyebrows, and/or temples is possible. Instead of the coupling portion being configured to be located, or routed above the top of the patient's forehead, in at least one embodiment, the coupling portion can be configured to be located above the patient's head when the head tracker 50 is mounted on a patient's head.

Figure 14:
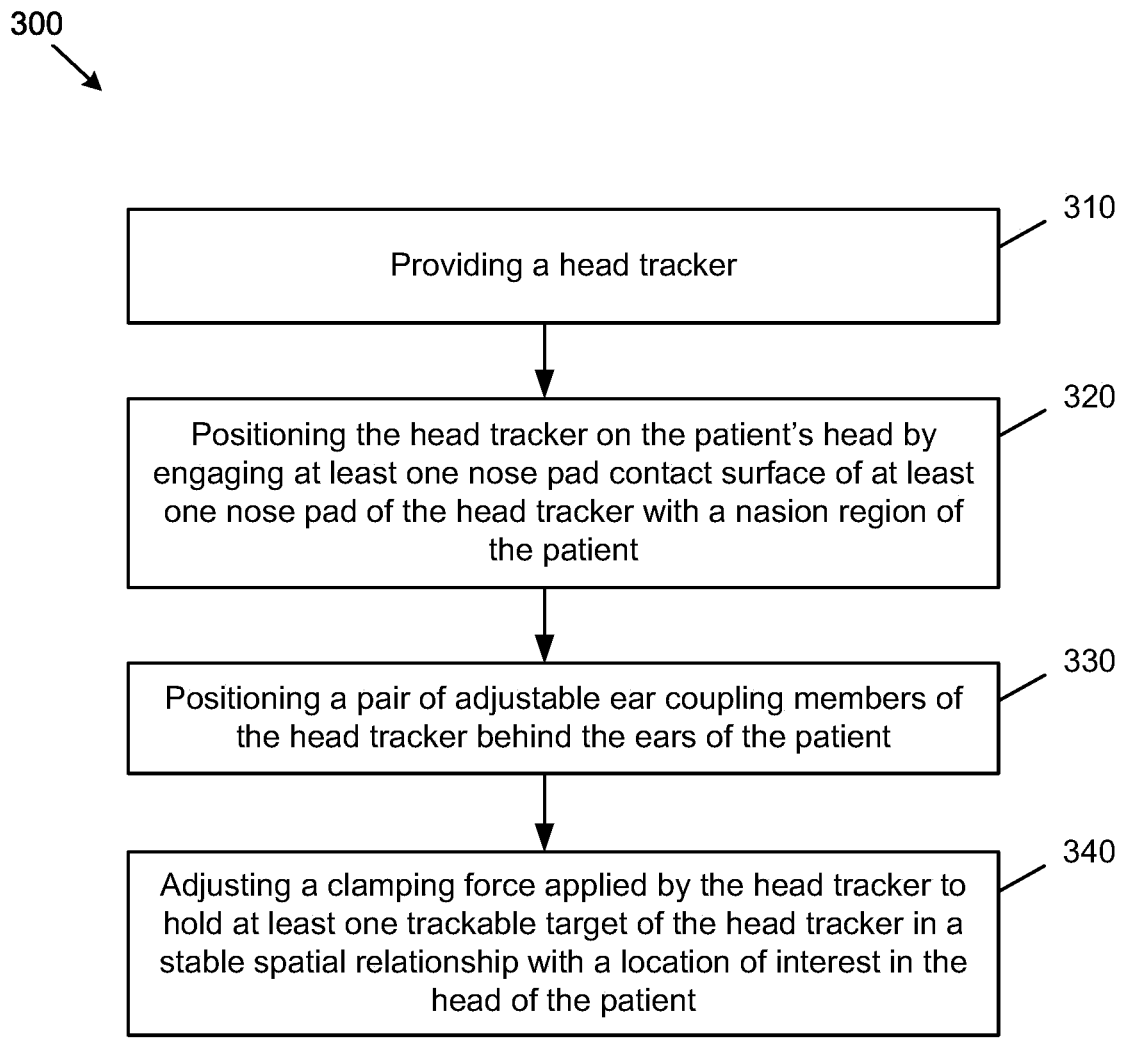
FIG. 14 is a flowchart of an example method of tracking a head of a patient.

Referring now to FIG. 14, shown therein is an example flowchart of a method 300 for tracking the head of a patient.

Method 300 can begin at act 310, in which a head tracker is provided. For example, the head tracker may be the head tracker 30 of FIGS. 1 to 7 or the head tracker 50 of FIGS. 10 to 13. The head tracker includes at least one nose pad, such as nose pads 140, 240, a pair of adjustable ear coupling members, such as adjustable ear coupling members 150, 250, attached to the at least one nose pad, and at least one trackable target, such as trackable targets 130, 230. The at least one nose pad defines at least one nose pad contact surface, such as nose pad contact surfaces 142, 242.

At act 320 of method 300, the head tracker is positioned on the patient's head 40 by engaging the at least one nose pad contact surface with a nasion region 42 of the patient. In at least one embodiment, the at least one nose pad contact surface can be aligned with opposing sides of the nasion region 42 of the patient.

At act 330 of method 300, the pair of adjustable ear coupling members are positioned behind the ears of the patient. For example, the pair of adjustable ear coupling members can engage with the back surfaces 44 of the ears of the patient.

At act 340 of method 300, a clamping force applied by the head tracker is adjusted to hold the at least one trackable target in a stable spatial relationship with a location of interest in the head of the patient. The clamping force is configured to pull the nose pad rearwardly to hold the nose pad contact surface against the nasion region 42 of the patient and to pull the pair of adjustable ear coupling members forwardly to hold the ear coupling members against the back surfaces 44 of the ears of the patient.

In at least one embodiment, adjusting the head tracker can further involve configuring the clamping force applied by the head tracker to apply a rearward force that does not cause discomfort for the patient. When the patient's head is between 5th and 95th percentiles in each of width, length, and height dimensions for an adult head, adjusting the head tracker so that the clamping force applied by the head tracker applies a rearward force that does not cause discomfort for the patient can involve applying a rearward force within a range of about 1 to 4 Newtons against the nasion region of the patient.

In at least one embodiment, the head tracker can include at least one head cushion, such as head cushions 120 of head tracker 30. In such cases, the method 300 can also involve engaging at least a portion of the patient's head with the at least one head cushion.

In at least one embodiment, the method 300 can further include determining a position of a location of interest in the head of the patient by operating a motion tracking system to track the at least one trackable target and to determine a position and orientation of the at least one trackable target. From the position and orientation of the at least one trackable target as well as the stable spatial relationship between the at least one trackable target and the location of interest in the head of the patient, the position of the location of interest in the head of the patient can be determined. The motion tracking system for tracking the at least one trackable target can be, for example, motion tracking system 20. The motion tracking system can be an optical tracking system for optically tracking the at least one trackable target.

Various embodiments have been described herein by way of example only. Various modification and variations may be made to these example embodiments without departing from the spirit and scope of the invention, which is limited only by the appended claims.

The invention claimed is:

1. A system for tracking a head of a patient, the system comprising:
 (a) a head tracker comprising:
  i. a frame comprising a front arm and two side arms, the two side arms being spaced apart to accommodate the width of the patient's head between the side arms;
  ii. at least one trackable target coupled to the frame, a position and orientation of the at least one trackable target being determinable by a motion tracking system tracking the target;
  iii. at least one nose pad coupled to the front arm of the frame, defining at least one nose pad contact surface for engaging with a nasion region of the patient; and
  iv. a pair of adjustable ear coupling members shaped for engaging with at least a portion of a back surface of an ear of the patient, each ear coupling member being coupled to a respective side arm;
  wherein
   the head tracker is configured to apply a clamping force to pull the at least one nose pad rearwardly to hold the nose pad contact surface against the nasion region of the patient and to pull the pair of adjustable ear coupling members forwardly to hold the ear coupling members against the back surfaces of the ears of the patient, to hold the at least one trackable target in a stable spatial relationship with a location of interest in the head of the patient; and
 (b) the motion tracking system, wherein the motion tracking system comprises a sensor for tracking the at least one trackable target and a processor configured for determining a position of the location of interest in the head of the patient from the position and orientation of the at least one trackable target of the head tracker and the stable spatial relationship.

2. The system of claim 1, wherein the frame is configured to not overlay each of the patient's eyes, eyebrows, and temples when the head tracker is mounted on the patient's head.

3. The system of claim 2, wherein the frame comprises a junction at which each of the front arm and two side arms are coupled, wherein the two side arms extend from the junction substantially opposite directions, and the front arm extends from the junction substantially perpendicular to each of the two side arms.

4. The system of claim 3, wherein the junction is located above the top of the patient's head or the patient's forehead when the head tracker is mounted on the patient's head.

5. The system of claim 1, wherein:
the frame further comprises an adjusting mechanism that extends between the front arm and the two side arms for adjusting a pose of at least a portion of the front arm relative to the two side arms; and
adjusting the pose of the portion of the front arm varies a distance between the at least one nose pad and at least one ear coupling member of the pair of ear coupling members.

6. The system of claim 1, wherein:
the frame further comprises a hinge for coupling at least a portion of the front arm to the two side arms; and
rotation of the at least a portion of the front arm around the hinge is configured to vary a distance between the at least one nose pad and at least one ear coupling member of the pair of ear coupling members.

7. The system of claim 1, wherein the frame further comprises at least one head cushion coupled to at least one side arm of the two side arms for engaging with at least a portion of the patient's head when the head tracker is mounted on the patient's head.

8. The system of claim 7, wherein the at least one head cushion comprises a material that is deformable to enable the head cushion to adapt its surface to the shape of the at least a portion of the patient's head and that can resist a deformation following the application and immediate removal of a force of up to about 5 Newtons to the side arm.

9. The system of claim 1, wherein the clamping force applied by the head tracker is adjustable such that a distance between the position of the location of interest determined by the motion tracking system and the actual location of interest in the head varies by less than 1 millimeter when the head tracker is mounted on the patient's head and at least one of the patient's facial expression changes and the patient's mouth moves.

10. The system of claim 1, wherein the clamping force applied by the head tracker is adjustable such that a distance between the position of the location of interest determined by the motion tracking system and the actual location of interest in the head varies by less than 1 millimeter following the application and immediate removal of a force of up to about 5 Newtons to any part of the frame in any direction when the head tracker is mounted on the patient's head.

11. The system of claim 1, wherein the clamping force applied by the head tracker is configurable to apply a rearward force in the range of about 1 to 4 Newtons against the nasion region of the patient when the head tracker is mounted on the patient's head and when the patient's head is between $5^{th}$ and $95^{th}$ percentiles in each of width, length, and height dimensions for an adult head.

12. The system of claim 1, wherein the head tracker further comprises, for each side arm, a biasing member for applying the clamping force, the biasing member comprising at least one of an elastic member and a spring member.

13. The system of claim 1, wherein each adjustable ear coupling member comprises rubber padding defining at least one ear coupling contact surface for engaging with the at least a portion of a back surface of the ear of the patient.

14. The system of claim 1, wherein the at least one nose pad comprises at least two adjustable nose pads, an orientation of each nose pad being independently adjustable relative to the frame.

15. The system of claim 1, wherein the frame further comprises a nose pad attachment member that extends between the at least one nose pad and the front arm for adjustably coupling the at least one nose pad to the front arm, the at least one nose pad being coupled to the front arm by the nose pad attachment member.

16. The system of claim 15, wherein the nose pad attachment member comprises a pliable metal wire.

17. The system of claim 1, wherein the at least one trackable target coupled to the frame comprises at least one high contrast optical target marked on a surface of at least one of the front arm and the two side arms.

18. A method for tracking a head of a patient, the method comprising:
i. providing a head tracker comprising a frame, at least one nose pad coupled to the frame, a pair of adjustable ear coupling members coupled to the frame, and at least one trackable target coupled to the frame, the at least one nose pad defining at least one nose pad contact surface;
ii. positioning the head tracker on the patient's head by engaging the at least one nose pad contact surface with a nasion region of the patient;
iii. positioning the pair of adjustable ear coupling members behind the ears of the patient; and
iv. adjusting a clamping force applied by the head tracker to hold the at least one trackable target in a stable spatial relationship with a location of interest in the head of the patient, the clamping force being configured to pull the nose pad rearwardly to hold the nose pad contact surface against the nasion region of the patient and to pull the pair of adjustable ear coupling members forwardly to hold the ear coupling members against the back surfaces of the ears of the patient.

19. The method of claim 18, further comprising:
determining a position and orientation of the at least one trackable target by operating a motion tracking system to track the at least one trackable target; and
determining a position of the location of interest in the head of the patient from the position and orientation of the at least one trackable target of the head tracker and the stable spatial relationship.

20. The system of claim 6, wherein the hinge is a part of the front arm.

* * * * *